(12) United States Patent
Mizuyoshi et al.

(10) Patent No.: US 8,858,429 B2
(45) Date of Patent: Oct. 14, 2014

(54) LIGHTING DEVICE FOR ENDOSCOPE AND ENDOSCOPE DEVICE

(75) Inventors: Akira Mizuyoshi, Kanagawa (JP); Takaaki Saito, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 13/382,282

(22) PCT Filed: Jul. 5, 2010

(86) PCT No.: PCT/JP2010/061432
§ 371 (c)(1),
(2), (4) Date: Jan. 4, 2012

(87) PCT Pub. No.: WO2011/004801
PCT Pub. Date: Jan. 13, 2011

(65) Prior Publication Data
US 2012/0116159 A1 May 10, 2012

(30) Foreign Application Priority Data
Jul. 6, 2009 (JP) .............................. P2009-159962

(51) Int. Cl.
*A61B 1/06* (2006.01)

(52) U.S. Cl.
CPC ............. *A61B 1/0653* (2013.01); *A61B 1/0638* (2013.01); *A61B 1/0684* (2013.01)
USPC ............................ 600/180; 600/118; 600/178

(58) Field of Classification Search
CPC ............. A61B 1/00638; A61B 1/0653; A61B 1/0684; A61B 1/043
USPC ................... 600/178, 180, 182, 118; 362/574
See application file for complete search history.

(56) References Cited

U.S. PATENT DOCUMENTS

| 4,706,657 A | 11/1987 | Miyagi |
| 4,746,974 A | 5/1988 | Matsuo |
| 5,029,016 A * | 7/1991 | Hiyama et al. ................ 358/403 |

(Continued)

FOREIGN PATENT DOCUMENTS

| EP | 1 488 732 A1 | 12/2004 |
| EP | 1795798 | 6/2007 |

(Continued)

OTHER PUBLICATIONS

Japanese Office Action dated Feb. 5, 2013, with English translation.

(Continued)

*Primary Examiner* — John P Leubecker
(74) *Attorney, Agent, or Firm* — McGinn IP Law Group, PLLC

(57) ABSTRACT

A lighting device includes first and second light sources, a wavelength converting member and a light quantity ratio changing unit. A first light source uses a semiconductor light emitting device as an emission source. A second light source uses, as an emission source, a semiconductor light emitting device of a different emission wavelength from the first light source. A wavelength converting member is excited for light emission by light emitted from at least one of the first light source and the second light source. The light quantity ratio changing unit changing a light quantity ratio between the light emitted from the first light source and the light emitted from the second light source.

17 Claims, 24 Drawing Sheets

(56) References Cited

U.S. PATENT DOCUMENTS

| | | | |
|---|---|---|---|
| 5,282,030 A | 1/1994 | Nishimura et al. | |
| 5,749,830 A * | 5/1998 | Kaneko et al. | 600/160 |
| 5,894,322 A * | 4/1999 | Hamano et al. | 348/68 |
| 6,577,073 B2 * | 6/2003 | Shimizu et al. | 315/246 |
| 6,712,756 B1 | 3/2004 | Kura et al. | |
| 6,749,562 B2 * | 6/2004 | Nakamura et al. | 600/181 |
| 7,005,679 B2 * | 2/2006 | Tarsa et al. | 257/89 |
| 7,704,206 B2 | 4/2010 | Suzuki et al. | |
| 7,791,092 B2 * | 9/2010 | Tarsa et al. | 257/98 |
| 7,857,751 B2 * | 12/2010 | Iketani et al. | 600/109 |
| 7,969,097 B2 * | 6/2011 | Van De Ven | 315/112 |
| 8,038,317 B2 * | 10/2011 | Van De Ven et al. | 362/231 |
| 8,169,470 B2 | 5/2012 | Ishihara et al. | |
| 8,193,735 B2 * | 6/2012 | Wei et al. | 315/294 |
| 8,231,526 B2 | 7/2012 | Yabe et al. | |
| 2002/0070681 A1 * | 6/2002 | Shimizu et al. | 315/246 |
| 2003/0176768 A1 | 9/2003 | Gono et al. | |
| 2005/0010081 A1 | 1/2005 | Doguchi et al. | |
| 2005/0194876 A1 | 9/2005 | Shimada et al. | |
| 2006/0022214 A1 | 2/2006 | Morgan et al. | |
| 2006/0152926 A1 | 7/2006 | Hama et al. | |
| 2006/0178565 A1 | 8/2006 | Matsui et al. | |
| 2006/0256191 A1 * | 11/2006 | Iketani et al. | 348/65 |
| 2007/0282169 A1 * | 12/2007 | Tsujita | 600/160 |
| 2008/0017787 A1 | 1/2008 | Okawa et al. | |
| 2008/0205477 A1 * | 8/2008 | Hama et al. | 372/98 |
| 2008/0208006 A1 | 8/2008 | Farr | |
| 2008/0262316 A1 * | 10/2008 | Ajima et al. | 600/178 |
| 2008/0281154 A1 | 11/2008 | Gono et al. | |
| 2008/0283770 A1 | 11/2008 | Takahashi | |
| 2008/0294105 A1 | 11/2008 | Gono et al. | |
| 2009/0036743 A1 | 2/2009 | Yabe et al. | |
| 2009/0040598 A1 * | 2/2009 | Ito | 359/332 |
| 2009/0058999 A1 * | 3/2009 | Gono et al. | 348/71 |
| 2009/0062617 A1 * | 3/2009 | Mizuyoshi | 600/178 |
| 2009/0167149 A1 | 7/2009 | Ito | |
| 2009/0203966 A1 * | 8/2009 | Mizuyoshi | 600/182 |
| 2009/0306478 A1 * | 12/2009 | Mizuyoshi | 600/178 |
| 2010/0119110 A1 | 5/2010 | Kanda | |
| 2010/0141747 A1 | 6/2010 | Kubo et al. | |
| 2010/0280322 A1 * | 11/2010 | Mizuyoshi | 600/178 |
| 2011/0034770 A1 | 2/2011 | Endo | |
| 2011/0077465 A1 | 3/2011 | Mizuyoshi et al. | |
| 2011/0237895 A1 | 9/2011 | Yoshida et al. | |
| 2012/0116159 A1 | 5/2012 | Mizuyoshi et al. | |

FOREIGN PATENT DOCUMENTS

| | | |
|---|---|---|
| EP | 2 020 202 A2 | 2/2009 |
| EP | 2 130 484 A1 | 12/2009 |
| EP | 2 301 413 A1 | 3/2011 |
| EP | 2 301 418 A1 | 3/2011 |
| JP | S62-183293 A | 8/1987 |
| JP | 63-155984 A | 6/1988 |
| JP | H 4-314181 A | 11/1992 |
| JP | 6-040174 B | 5/1994 |
| JP | 2001-137172 A | 5/2001 |
| JP | 2002-95635 A | 4/2002 |
| JP | 3583731 B2 | 1/2004 |
| JP | 2005-006856 A | 1/2005 |
| JP | 2005-122237 A | 5/2005 |
| JP | 2005-124823 A | 5/2005 |
| JP | 2005-198794 A | 7/2005 |
| JP | 2005-279255 A | 10/2005 |
| JP | 2006-2115 | 1/2006 |
| JP | 2006-006968 A | 1/2006 |
| JP | 2006-12235 A | 5/2006 |
| JP | 2006-173324 A | 6/2006 |
| JP | 2006-212335 A | 8/2006 |
| JP | A-2006-341077 | 12/2006 |
| JP | 2007-139822 A | 6/2007 |
| JP | 2007-252809 A | 10/2007 |
| JP | 2008-284030 A | 1/2008 |
| JP | 2009-25401 A | 2/2009 |
| JP | 2009-34224 A | 2/2009 |
| JP | 2009-056248 A | 3/2009 |
| JP | 2009-153712 A | 7/2009 |
| JP | 2010-035922 A | 2/2010 |
| JP | 2010-113616 A | 5/2010 |
| JP | 2010-136748 A | 6/2010 |
| JP | 2011-10998 A | 1/2011 |
| JP | 2011-36361 A | 2/2011 |
| WO | WO 02/12127 A2 | 2/2002 |
| WO | WO 2005/104926 A1 | 1/2005 |
| WO | WO 2008/048688 A2 | 4/2008 |

OTHER PUBLICATIONS

Japanese Office Action dated Nov. 6, 2012, with English translation.
International Search Report in PCT/JP2010/061432 dated Sep. 28, 2010 (English Translation Thereof).
Extended European Search Report dated Jan. 24, 2013.
United States Office Action dated Jul. 10, 2013, in U.S. Appl. No. 12/853,903.
Japanese Office Action dated Jun. 4, 2013, with partial English translation.
European Search Report dated Dec. 6, 2012.
European Search Report dated Nov. 22, 2010.
Japanese Office Action dated Jun. 18, 2013 with English translation thereof.
United States Office Action dated Dec. 13, 2012, in U.S. Appl. No. 12/853,903.
Decision of Rejection dated Nov. 12, 2013, with partial English translation.
Chinese First Office Action dated Nov. 13, 2013, with English translation.
Japanese Office Action dated Apr. 22, 2014 with a partial English translation.
European Office Action dated May 21, 2014.
JP-OA 2009-159962 Pretrial Reexamination Report prepared by JPO on Mar. 14, 2014.
U.S. Office Action for U.S. Appl. No. 12/853,903 dated Jul. 15, 2014.
U.S. Office Action for Co-Pending U.S. Appl. No. 13/562,149 dated Aug. 12, 2014.

* cited by examiner

WHITE LIGHT OBSERVATION IMAGE

NARROW BAND LIGHT OBSERVATION IMAGE

FIG. 18

|  | LIGHT QUANTITY RATIO | |
|  | λa | λb |
| --- | --- | --- |
| OPERATOR A | 60% | 40% |
| OPERATOR B | 75% | 25% |
| OPERATOR C | 50% | 50% |
| ⋮ | ⋮ | ⋮ |

FIG. 21

| LIGHT QUANTITY RATIO ($\lambda a : \lambda b$) | COLOR CONVERSION FACTOR TABLE | | |
|---|---|---|---|
| | $K_R$ | $K_G$ | $K_B$ |
| 100 : 0 | R00 | G00 | B00 |
| 99 : 1 | R01 | G01 | B01 |
| 98 : 2 | R02 | G02 | B02 |
| ⋮ | ⋮ | ⋮ | ⋮ |
| 0 : 100 | R100 | G100 | B100 |

LIGHTING DEVICE FOR ENDOSCOPE AND ENDOSCOPE DEVICE

CROSS-REFERENCE TO RELATED APPLICATIONS

This application claims the benefit of Japanese Patent Application No. 2009-159962, filed on Jul. 6, 2009, the entire contents of which are hereby incorporated by reference, the same as if set forth at length, the entire of which are incorporated herein by reference.

TECHNICAL FIELD

The present invention relates to a lighting device for an endoscope and an endoscope device.

BACKGROUND ART

In a general endoscope device, light emitted from a lamp of a light source system is guided to an endoscope tip portion by a light guide provided inside an endoscope insertion section to be inserted into a subject and is emitted through an illuminating window disposed in the endoscope tip portion, and thus, an observation site of the subject is illuminated. White light is used for observation of general organism tissues, but in recent years, an endoscope device capable of enhancing a state of a mucosal tissue through irradiation with light of a wavelength of a specific narrow band or capable of special light observation for observing autofluorescence of a fluorescent material precedently administered is utilized (Patent Documents 1 and 2). When such a type of endoscope device is used, since organism tissue is irradiated with special light, neovascular generated in a mucosal layer or a submucosal layer may be observed, and hence, a microstructure of a mucosal surface not obtained in a general observation image may be described.

In Patent Documents 1 and 2 mentioned above, merely a specific wavelength band of light emitted from a white light source such as a xenon lamp is taken out by using a color filter so as to be used as the special light. It is noted that a laser light source may be used as the white light source apart from the xenon lamp, and a light emitting apparatus for generating white light through a combination of, for example, a blue laser light source and a phosphor causing excitation emission by using a blue laser beam as excitation light has been proposed (Patent Document 3).

The endoscope device of each of Patent Documents 1 and 2, however, employs a structure in which the light emitted from the white light source is divided on a time basis by a color filter so as to frame-sequentially emit light of different wavelength bands (of, for example, R, G and B). Therefore, it is necessary to synthesize captured images of a plurality of frames (of R, G and B) for obtaining a full-color observation image, which prevents increase of the frame rate of an observation image. Furthermore, since the illumination light is generated through light absorption with the color filter, the quantity of light is unavoidably reduced, which is a factor to increase a noise component of the observation image. Although it is possible to increase the sensitivity by reducing the frame rate, a resultant image is easily blurred in this case.

On the other hand, in diagnosis with special light, tissue information of, for example, a surface layer portion or a portion toward a deep layer portion of organism tissue is a significant observation target. In regard to, for example, a cancer of a digestive organ, tumor vessels appear in a mucosal surface layer portion at an early stage, and the tumor vessels are found to expand, meander and increase in the density as compared with general blood vessels appearing in the surface layer portion. Therefore, the kind of tumor may be identified by dissecting the characters of the vessels. In the aforementioned endoscope device using a color filter, however, when tissue information of a surface layer portion of organism tissue in particular, for example, is desired to observe, it is difficult to restrict the transmission wavelength band of the color filter to a specific narrow band, and in addition, the illumination light of the restricted narrow band may not be obtained in a sufficient quantity, and therefore, the image quality of an observation image is disadvantageously degraded.

PRIOR ART DOCUMENTS

Patent Documents

Patent Document 1: Japanese Patent No. 3583731
Patent Document 2: Japanese Patent Publication No. 6-40174-B
Patent Document 3: Japanese Laid-Open Patent Publication No. 2006-173324-A

DISCLOSURE OF THE INVENTION

Problem to be Solved by the Invention

An object of the invention is providing a lighting device for an endoscope and an endoscope device capable of obtaining desired tissue information of organism tissue in a clearer state suitable to diagnosis in observation of the organism tissue with white light or special light.

Means for Solving the Problem

The present invention includes the following:
(1) A lighting device for an endoscope obtaining illumination light by using light emitted from a plurality of light sources, including: a first light source that uses a semiconductor light emitting device as an emission source; a second light source that uses, as an emission source, another semiconductor light emitting device of a different emission wavelength from the first light source; a wavelength converting member that is excited for light emission by light emitted from at least one of the first and second light sources; and light quantity ratio changing means that changes a light quantity ratio between the light emitted from the first light source and the light emitted from the second light source.
(2) An endoscope device including an illuminating optical system that emits illumination light from the aforementioned lighting device for an endoscope from a tip of an endoscope insertion section; and an imaging optical system that includes an imaging device that receives light from an illuminated region irradiated with the illumination light and that outputs a picture signal.

Effects of the Invention

According to the lighting device for an endoscope and the endoscope device of the present invention, desired tissue information of organism tissue may be obtained in a clearer state suitable to diagnosis in observation of the organism tissue with white light or special light of a specific wavelength band.

BRIEF DESCRIPTION OF DRAWINGS

FIG. 18 This is an explanatory diagram of a light quantity ratio table in which light quantity ratios for respective operators of the endoscope are registered.

FIG. 21 This is an explanatory diagram illustrating a table of color conversion factors listed correspondingly to the light quantity ratios.

MODE FOR CARRYING OUT THE INVENTION

Now, a preferred embodiment of the invention will be described in detail with reference to the accompanying drawings.

Figure 1:
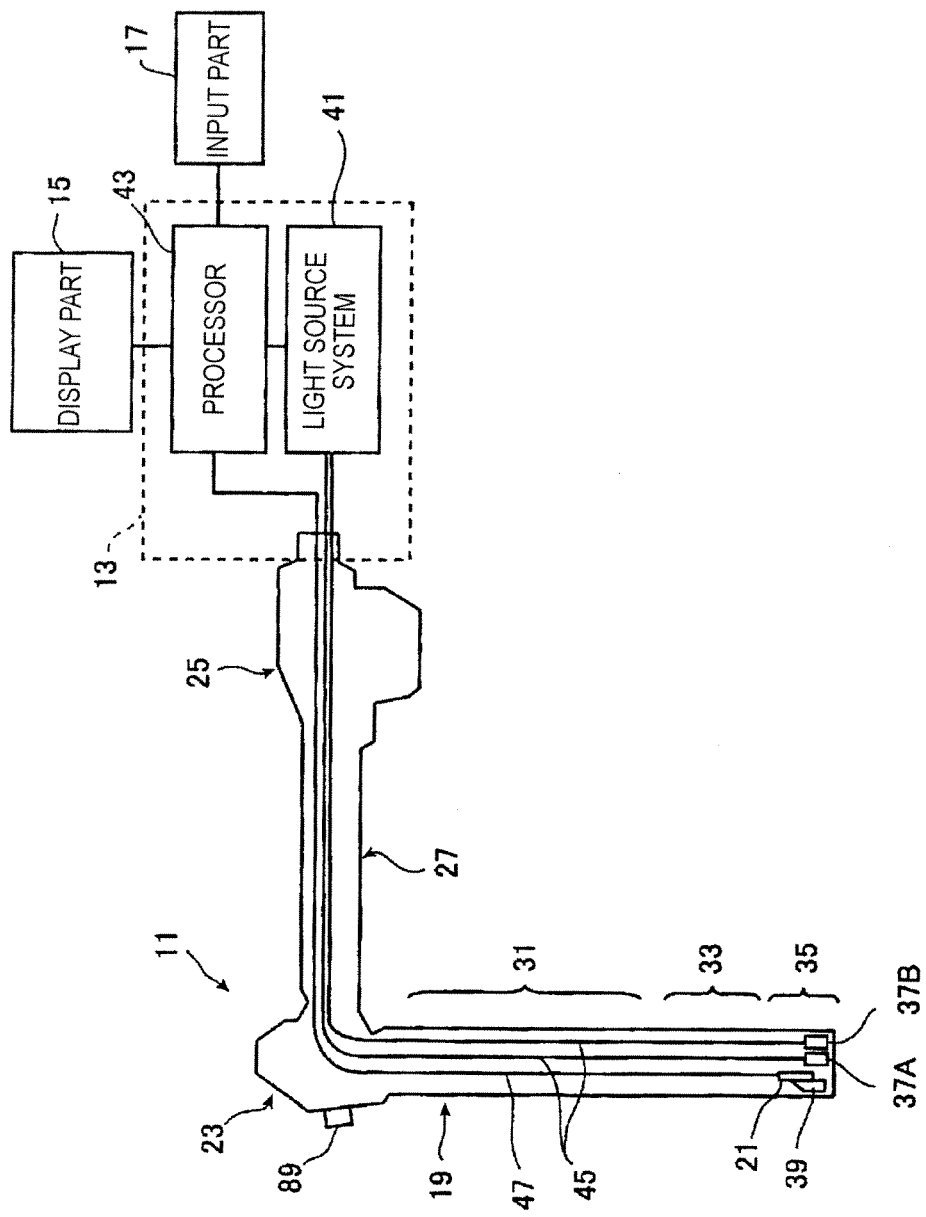
FIG. 1 This is a schematic diagram of an endoscope device using a lighting device for an endoscope used for describing an embodiment of the invention.
Figure 2:
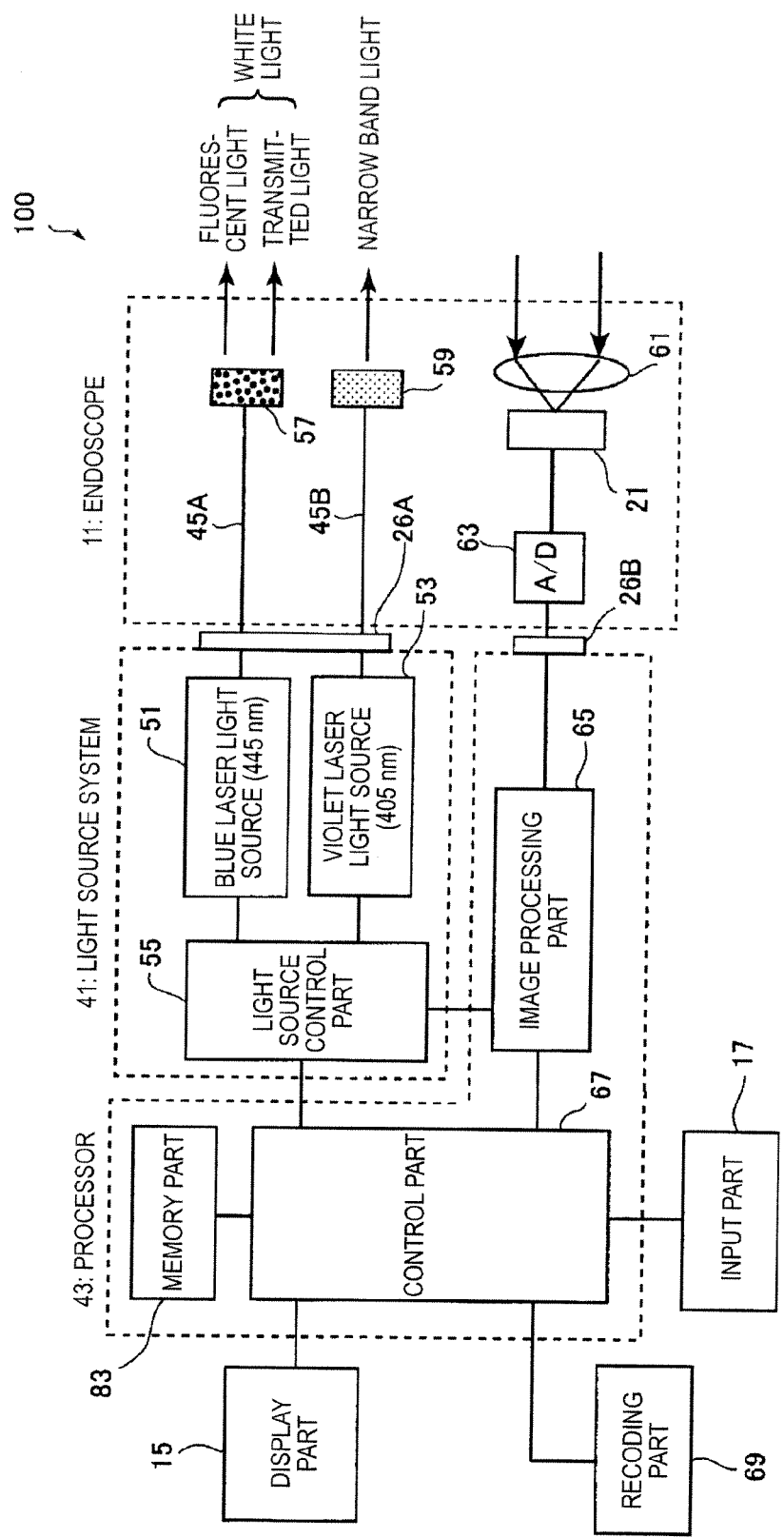
FIG. 2 This is a block diagram of the endoscope device of FIG. 1.

FIG. 1 is a schematic diagram of an endoscope device using a lighting device for an endoscope used for describing an embodiment of the invention, and FIG. 2 is a block diagram of the endoscope device of FIG. 1.

The endoscope device 100 of FIG. 1 includes an endoscope 11 and a control unit 13 connected to the endoscope 11. The control unit 13 is connected to a display part 15 for displaying image information and the like and an input part 17 for accepting an input operation. The endoscope 11 is an electronic endoscope including an illuminating optical system for emitting illumination light from a tip of an endoscope insertion section 19 and an imaging optical system including an imaging device for capturing an image of an observation target region.

The endoscope 11 includes the endoscope insertion section 19 to be inserted into a subject; an operation section 23 for conducting a bending operation of the tip of the endoscope insertion section 19 and conducting operations such as suction, air supply, water supply and the like from the tip of the endoscope insertion section 19; a connector 25 for removably connecting the endoscope 11 to the control unit 13; and a universal cord section 27 for connecting the operation section 23 and the connector 25 to each other. Although not shown in the drawings, various channels including a clamp channel through which a tool for picking a tissue or the like is inserted and channels for supplying air and water are provided inside the endoscope 11.

The endoscope insertion section 19 includes a soft portion 31 with flexibility, a bending portion 33 and a tip portion (hereinafter also referred to as the endoscope tip portion) 35. In the endoscope tip portion 35, illuminating ports 37A and 37B through which an observation target region is irradiated with light and an imaging device 21 such as a CCD (charge coupled device) image sensor or a CMOS (complementary metal-oxide semiconductor) image sensor for obtaining image information of the observation target region are provided. The imaging device 21 may be a primary color type imaging device with sensitivity to R (red), G (green) and B (blue) or a complementary color type imaging device with sensitivity to C (cyan), M (magenta) and Y (yellow) or to C, M, Y and G. It is noted that the imaging device 21 is provided with an image forming member 39 such as an objective lens.

The bending portion 33 is provided between the soft portion 31 and the tip portion 35 and is bendable through, for example, a wire operation conducted by the operation section 23 or an operation conducted by activating an actuator. This bending portion 33 may be bent to an arbitrary direction at an arbitrary angle in accordance with a site or the like of a subject for which the endoscope 11 is used, so as to make the illuminating ports 37A and 37B of the endoscope tip portion 35 and an observation direction of the imaging device 21 face toward a desired observation site. Furthermore, although not shown in the drawing, the illuminating ports 37A and 37B of the endoscope insertion section 19 are provided with a cover glass and a lens.

The control unit 13 includes a light source system 41 for generating the illumination light to be supplied to the illuminating ports 37A and 37B of the endoscope tip portion 35; and a processor 43 for performing image processing of picture signals supplied from the imaging device 21, and is connected to the display part 15 and the input part 17. The processor 43 performs the image processing of picture signals transmitted from the endoscope 11 on the basis of an instruction given from the operation section 23 of the endoscope 11 or the input part 17, so as to generate display images and to supply the generated images to the display part 15.

Optical fibers 45A and 45B for guiding the illumination light from the light source system 41 and a scope cable 47 for connecting the imaging device 21 and the processor 43 to each other are inserted through the endoscope 11. Furthermore, although not shown in the drawings, various signal lines extending from the operation section 23 and tubes of air supply and water supply channels and the like are also connected to the control unit 13 and the like through the universal cord section 27 via the connector 25. The connector 25 on the side of the endoscope 11 is removably connected to the connector parts 26A and 26B respectively provided on the light source system 41 and the processor 43 as illustrated in FIG. 2.

The light source system 41 includes, as emission sources, a blue laser light source (a first light source) 51 with a center wavelength of 445 nm and a violet laser light source (a second light source) 53 with a center wavelength of 405 nm as illustrated in FIG. 2. Beams emitted from semiconductor light emitting devices of the light sources 51 and 53 are individually controlled by alight source control part 55, so that alight quantity ratio between light emitted from the blue laser light source 51 and light emitted from the violet laser light source 53 may be freely changed.

For the blue laser light source 51 corresponding to the first light source and the violet laser light source 53 corresponding to the second light source, a broad area type InGaN-based laser diode may be used, or alternatively an InGaNAs-based laser diode or a GaNAs-based laser diode may be used. Furthermore, a luminous element such as a light emitting diode may be used as the light source.

The laser beams emitted from the light sources 51 and 53 are input to the optical fibers by condensing lenses (not shown) and are propagated to the endoscope tip portion 35 (see FIG. 1) of the endoscope 11 respectively by the optical fibers 45A and 45B through the connector part 26A and the connector 25 (see FIG. 1) on the side of the endoscope 11. Then, the laser beam emitted from the blue laser light source 51 irradiates a phosphor 57 corresponding to a wavelength converting member disposed in the endoscope tip portion 35, and the laser beam emitted from the violet laser light source 53 irradiates a light deflecting/diffusing member 59.

Each of the optical fibers 45A and 45B is a multimode fiber, and for example, a thin cable with a core diameter of 105 μm, a cladding diameter of 125 μm and a diameter φ including an outer cover of a protection layer of 0.3 to 0.5 mm may be used.

The phosphor 57 includes a plurality of kinds of phosphors (such as a YAG-based phosphor and a phosphor including BMA ($BaMgAl_{10}O_{27}$) or the like) that absorb a part of the blue laser beam emitted from the blue laser light source 51 and emit light of green to yellow through excitation. As a result, the excited light of green to yellow obtained from the excitation light of the blue laser beam emitted from the blue laser light source 51 and a part of the blue laser beam not absorbed by but passing through the phosphor 57 are combined so as to generate white (pseudo white) illumination light. When the semiconductor light emitting device is used as the excitation light source as in this exemplified structure, white light with high density may be obtained with high efficiency, and furthermore, the intensity of the white light may be easily adjusted. In addition, change of the white light in color temperature and chromaticity may be small.

Incidentally, as the blue laser light source 51, the phosphor 57 and the optical fiber 45A connecting them to each other, "Micro-White" (trade name) manufactured by Nichia Corporation may be used.

Furthermore, the light deflecting/diffusing member 59 may be a material capable of transmitting the laser beam emitted from the violet laser light source 53, and for example, a resin material with a translucent property, glass or the like is used. Moreover, the light deflecting/diffusing member 59 may employ a structure in which a light diffusing layer of fine irregularities or a mixture of particles (of a filler or the like) with different refractive indexes is provided on a surface or the like of a resin material or glass, or a structure using a translucent material. Thus, transmitted light outgoing from the light deflecting/diffusing member 59 becomes illumination light of a narrow band wavelength that attains a uniform light quantity in a prescribed irradiated region.

Incidentally, the phosphor 57 and the light deflecting/diffusing member 59 may prevent phenomenon such as superimpose of noise that may be an obstacle in imaging and occurrence of a flicker in displaying a dynamic image derived from speckle occurring due to coherence of laser beams. Furthermore, in consideration of a difference in the refractive index between a fluorescent material included in the phosphor 57 and a fixing/solidifying resin used as a filler, the phosphor 57 is preferably made of a fluorescent material itself and a particle diameter of the filler that little absorb but largely scatter light of the infrared region. Thus, a scattering effect may be increased without lowering the light intensity of light of the red region or the infrared region, there is no need to provide optical path changing means such as a concave lens and optical loss may be reduced.

Figure 3:
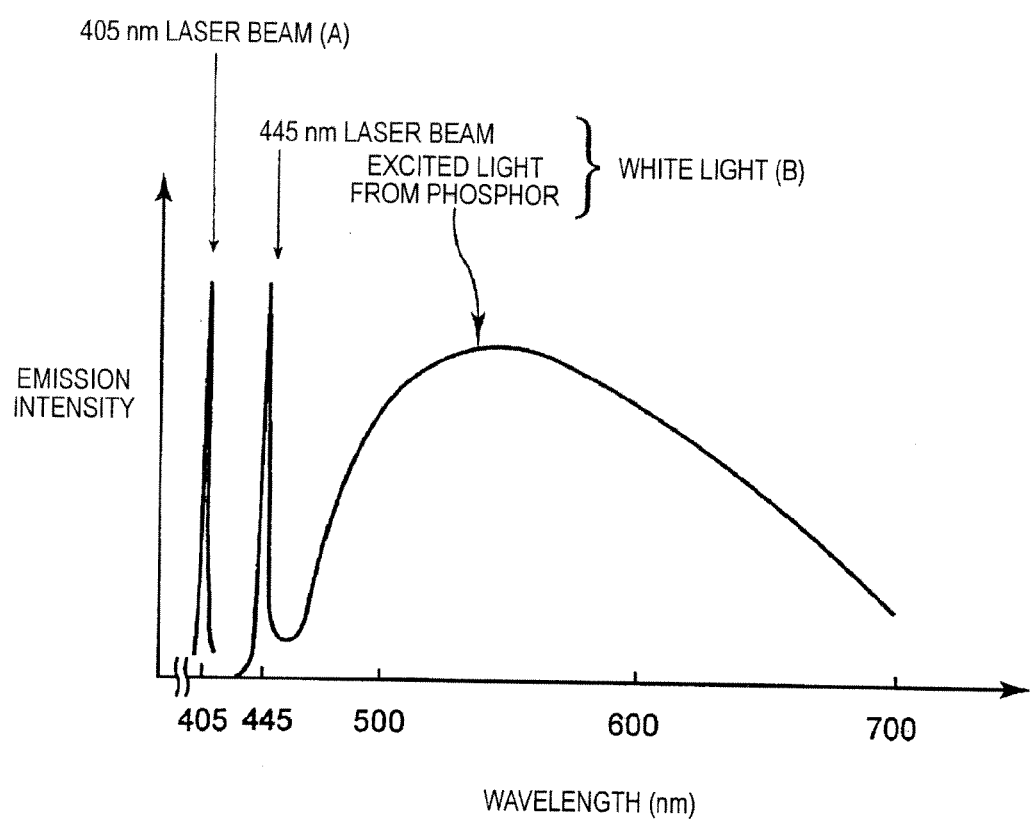
FIG. 3 This is a graph of emission spectra of a laser beam emitted from a violet laser light source, a blue laser beam emitted from a blue laser light source and light obtained by a phosphor through wavelength conversion of the blue laser beam.

FIG. 3 is a graph illustrating emission spectra of a laser beam emitted from the violet laser light source 53, a blue laser beam emitted from the blue laser light source 51 and light obtained from the blue laser beam through the wavelength conversion by the phosphor 57. The violet laser beam emitted from the violet laser light source 53 is expressed as an emission line with a center wavelength of 405 nm (i.e., a profile A). Furthermore, the blue laser beam emitted from the blue laser light source 51 is expressed as an emission line with a center wavelength of 445 nm, and the excited light obtained from the blue laser beam and emitted from the phosphor 57 exhibits a spectral intensity distribution having emission intensity increased in a wavelength band of approximately 450 to 700 nm (i.e., a profile B). Owing to the profile B of the excited light and the blue laser beam, the aforementioned white illumination light is generated.

The white light herein means not only light strictly including all wavelength components of visible light but also light including specific wavelength bands such as R, G and B, and includes, in a broad sense, light including a wavelength component from green to red, light including a wavelength component from blue to green, and the like.

Specifically, the illumination light is generated in this endoscope device 100 by relatively increasing/decreasing the emission intensities of the profile A and the profile B, and hence, illumination light having different characteristics may be obtained in accordance with a mixing ratio between the profiles A and B.

FIG. 2 will be referred to again for giving further description. The illumination light obtained by the combination of the blue laser light source 51 and the phosphor 57, and the violet laser light source 53 as described above is emitted from the tip portion of the endoscope 11 toward an observation target region of a subject. Then, a state of the observation target region irradiated with the illumination light is imaged by forming an image on the imaging device 21 by an imaging lens 61.

A picture signal output from the imaging device 21 after the imaging is converted into a digital signal by an A/D converter 63 and input to an image processing part 65 of the processor 43. In the image processing part 65, the input picture signal is converted into image data and subjected to appropriate image processing, so as to generate desired output image information. Then, the thus obtained image information is displayed through a control part 67 in the display part 15 as an endoscope observation image. Furthermore, the image information is recorded in a recording device 69 including a memory or a storage device if necessary.

The recording device 69 may be contained in the processor 43 or connected to the processor 43 through a network. Information on an endoscope observation image to be recorded in the recording device 69 is recorded in combination with information on a light quantity ratio employed in the imaging. Therefore, the recorded endoscope observation image may be accurately interpreted after the endoscopic observation, and furthermore, the image may be subjected to appropriate image processing such as standardization in accordance with the light quantity ratio, and thus, an application range of the endoscope observation image may be expanded. In particular, when spectral reflectance is estimated with the number of bands (R, G and B) increased in a pseudo manner on the basis of information on a plurality of images obtained with spectrally different light quantity ratios, color difference may be more finely separated.

Figure 4:
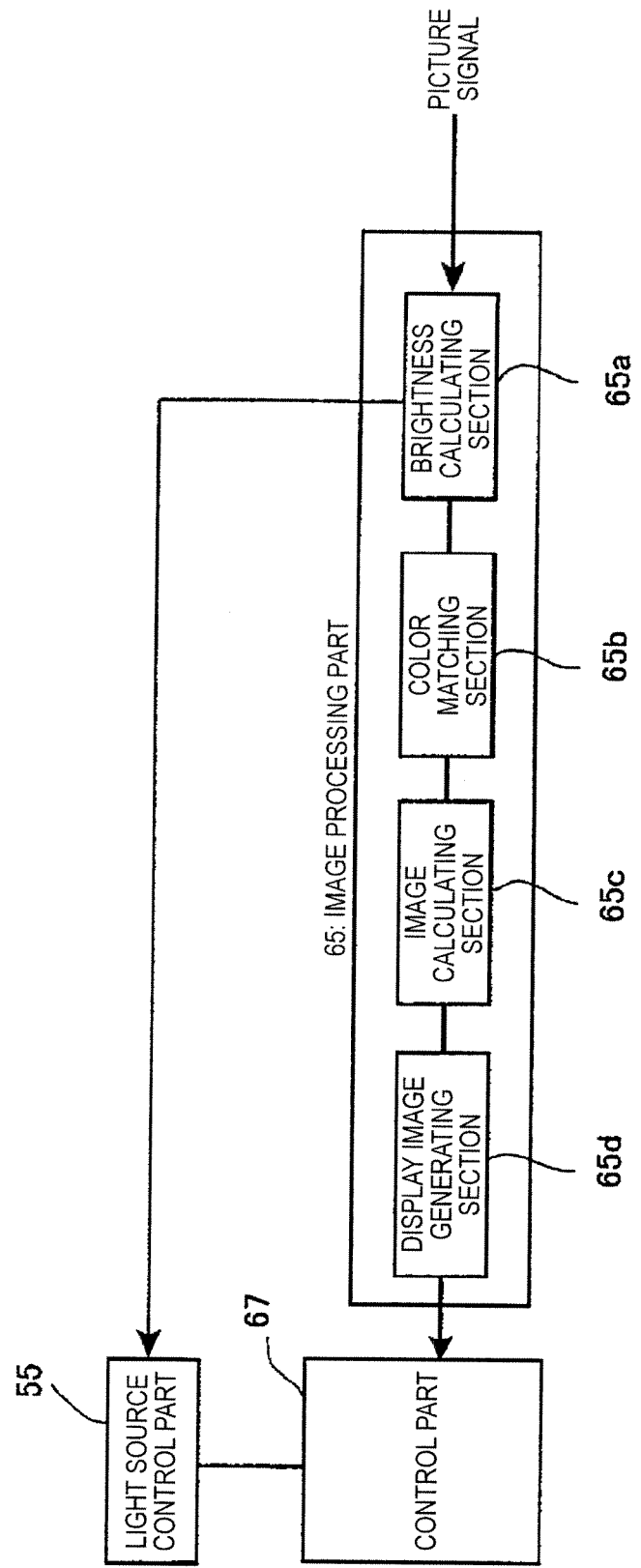
FIG. 4 This is a detailed block diagram of an image processing part.

FIG. 4 is a detailed block diagram of the image processing part. A picture signal input from the imaging device 21 to the image processing part 65 is first input to a brightness calculating section 65$a$. The brightness calculating section 65$a$ obtains brightness information of the picture signal such as the maximum brightness, the minimum brightness and screen average brightness, so as to normalize the brightness. Then, in the case where the brightness of the picture signal is too low or too high, it outputs a correction signal to the light source control part 55 for increasing/decreasing the quantities of light emitted from the light sources 51 and 53 so that the picture signal may attain a desired brightness level.

Next, a color matching section 65$b$ adjusts the normalized image data so that the image may attain desired color tone. For example, when the picture signal includes signals of the colors R, G and B, it adjusts intensity balance among the signals of the colors R, G and B. In the above-described light source system 41, the quantities of light emitted from the blue laser light source 51 and the violet laser light source 53 are respectively controlled by the light source control part 55, so that the light quantity ratio between the light emitted from the blue laser light source 51 and the light emitted from the violet laser light source 53 may be arbitrarily changed. Therefore, chromaticness and total illuminance of the illumination light are varied sometimes in accordance with the set light quantity ratio, and hence, the brightness calculating section 65$a$ and the color matching section 65$b$ correct a picture signal in accordance with the set light quantity ratio so as to retain the color tone and the brightness of an observation image at a prescribed constant level.

Then, an image calculating section 65$c$ performs image calculation precedently determined or requested, and supplies a result of the image calculation to a display image generating section 65$d$, where output image information is created and output to the control part 67.

Next, application of the aforementioned endoscope device 100 to observation of a blood vessel image of organism tissue surface layer will be described.

Figure 5:
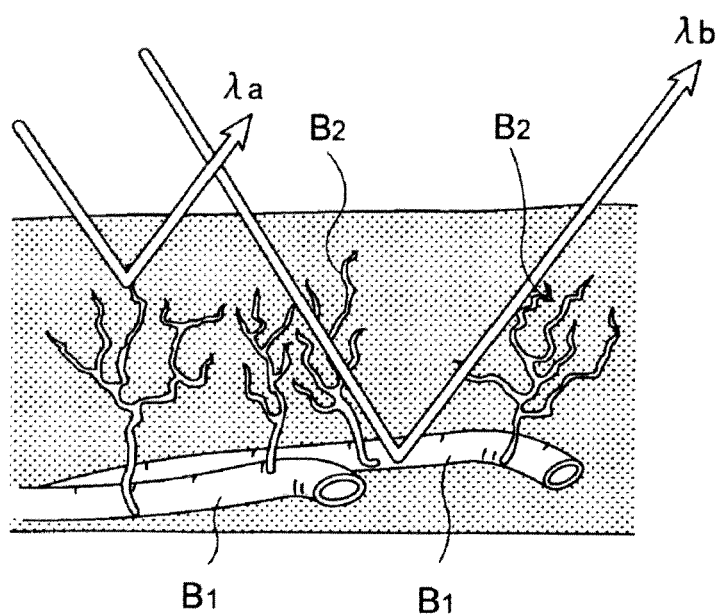
FIG. 5 This is an explanatory diagram schematically illustrating blood vessels of a mucosal surface layer of organism tissue.

FIG. 5 is an explanatory diagram schematically illustrating blood vessels of a mucosal surface layer of organism tissue. In the mucosal surface layer of the organism tissue, blood capillaries B2 such as dendritic vasoganglions are formed from a blood vessel B1 of a mucosal deep layer up to the mucosal surface layer, and it is reported that a lesion of the organism tissue appears in a microstructure of the blood capillaries B2 or the like. Therefore, in recent years, an image of blood capillaries of a mucosal surface layer enhanced by using light of a specific narrow band wavelength is observed by an endoscope device, so as to aim at early detection of a minute lesion or diagnosis of a lesion range.

When the illumination light enters the organism tissue, the incident light is propagated diffusely in the organism tissue, and since the absorption/diffusion characteristic of the organism tissue has wavelength dependency, light of a shorter wavelength tends to have a strong diffusing characteristic. In other words, the extent of spread of the light depends upon the wavelength of the illumination light. On the other hand, blood flowing through a blood vessel has a peak absorption and attains high contrast at a wavelength in the vicinity of 400 to 420 nm. For example, when the illumination light is in a wavelength band λa in the vicinity of a wavelength 400 nm, blood vessel information of blood capillaries of a mucosal surface layer may be obtained, and when it is in a wavelength band λb in the vicinity of a wavelength 500 nm, blood vessel information including blood vessels present in a deeper layer may be obtained. Therefore, for the observation of blood vessels of a surface layer of organism tissue, a light source with a center wavelength of 360 to 800 nm, preferably 365 to 515 nm and more preferably 400 to 470 nm is used.

Figure 6:
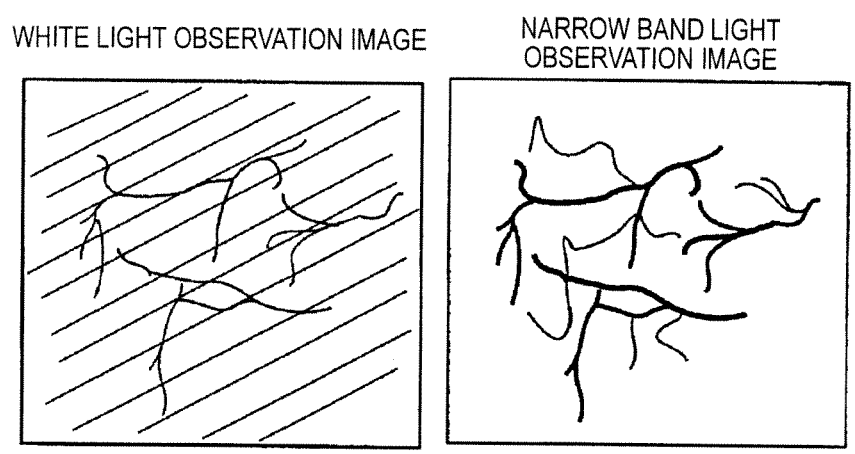
FIG. 6 This is an explanatory diagram illustrating schematic display examples of an observation image obtained by the endoscope device.

Accordingly, as illustrated in FIG. 6 as schematic display examples of an observation image obtained by an endoscope device, in an observation image obtained when the illumination light is white light, an image of blood vessels of a comparatively deep mucosal layer is obtained, and on the other hand, minute blood capillaries present in a mucosal surface layer are blurred. On the contrary, in an observation image obtained when the illumination light is narrow band light of a short wavelength alone, minute blood capillaries of a mucosal surface layer may be clearly seen.

In this exemplified structure, the light quantity ratio between the light emitted from the blue laser light source 51 with the center wavelength of 445 nm and the light emitted from the violet laser light source 53 with the center wavelength of 405 nm is freely changed by the light source control part 55 (see FIG. 2) of the endoscope device 100. The change of the light quantity ratio is conducted by operating, for example, a switch 89 provided on the operation section 23 of the endoscope 11 of FIG. 1, and thus, the image may be enhanced so that blood capillaries of a mucosal surface layer may be more easily observed. Specifically, when a blue laser beam component of the blue laser light source 51 occupies a larger ratio, the illumination light includes a white light component derived from the blue laser beam and the excited light generated by the phosphor 57 in a larger ratio, and hence, an observation image as the white light observation image of FIG. 6 may be obtained. However, since the blue laser beam, that is, narrow band light, is mixedly included in the illumination light, blood capillaries of the surface layer are enhanced in the observation image.

Alternatively, when a violet laser beam component of the violet laser light source 53 occupies a larger ratio, an observation image as the narrow band light observation image of FIG. 6 is obtained. When the light quantity ratio between the light emitted from the blue laser light source 51 and the light emitted from the violet laser light source 53 is increased/decreased, namely, when the ratio of the violet laser beam component in the whole illumination light components is increased/decreased, the minute blood capillaries of the mucosal surface layer may be continuously enhanced for the observation.

Accordingly, as the violet laser beam component occupies a larger ratio, the minute blood capillaries included in a thin depth region of the mucosal surface layer are clearly shown in the observation image, and as the ratio of the violet laser beam component is smaller, information of blood vessels included in a wide depth region spread from the mucosal surface layer to the deep layer is shown. Therefore, a blood vessel distribution along a depth direction from the mucosal surface layer may be displayed in a pseudo manner, and blood vessel information along the depth direction of an observation site may be extracted as continuous information corresponding to respective depth ranges. In particular, in this exemplified structure, the blood vessel information obtained by using the blue laser beam and the blood vessel information of the surface layer obtained by using the violet laser beam are both extracted, and since these information may be displayed as images to be compared with each other, the blood vessel information including blood vessels of a shallower surface layer portion that may not be observed by using the blue laser beam may be observed with increased visibility.

In the tip portion 35 (see FIG. 1) of the electronic endoscope where the imaging device 21 is disposed, a heat release value is increased in accordance with recent increase of pixels, increase of a frame rate and increase of power consumption, and hence, light that may be emitted from the tip portion 35 is also restricted. Under these circumstances, when the light quantity ratio between the light sources is changed so as to increase necessary light emission while suppressing the total light quantity of the illumination light, a problem, for example, that image processing alone is employed resulting in an image unavoidably having large noise may be overcome.

Figure 7A:
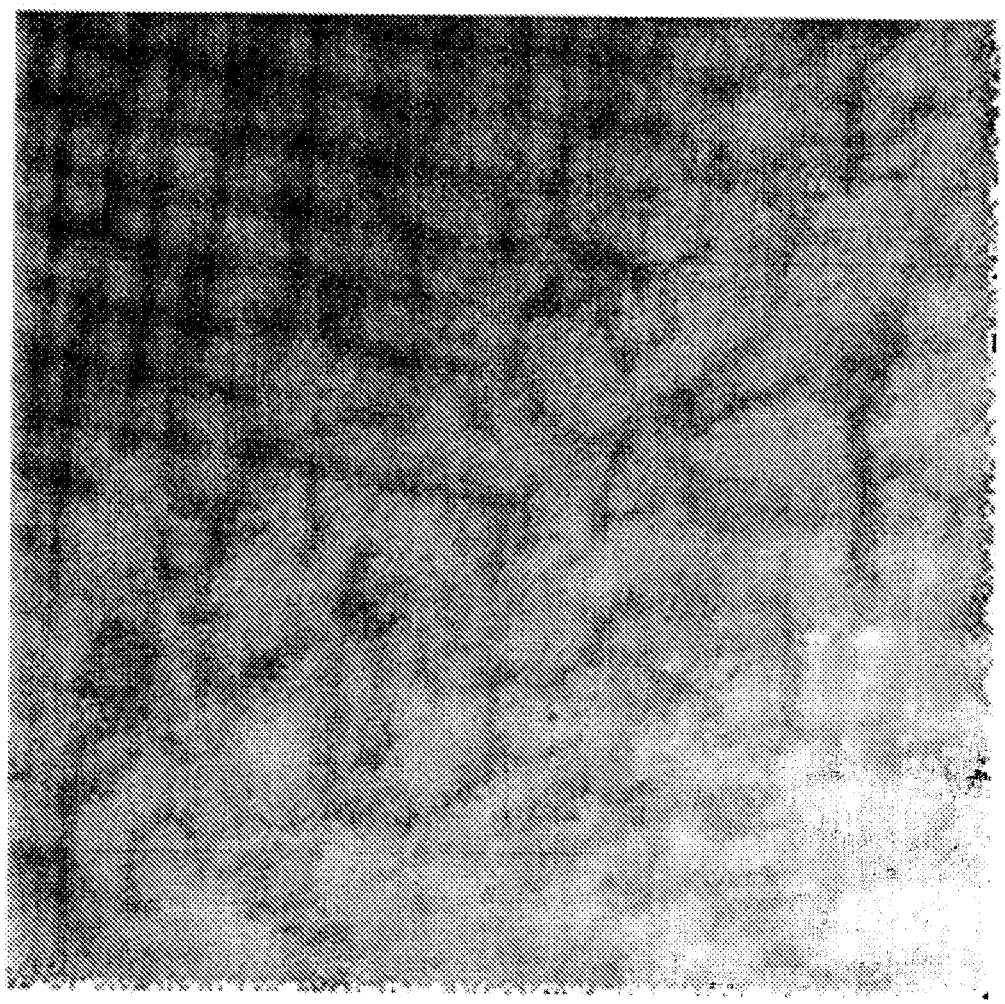
FIG. 7A This is an enlarged observation image of the inside of a lip observed by the endoscope device with white light.
Figure 7B:
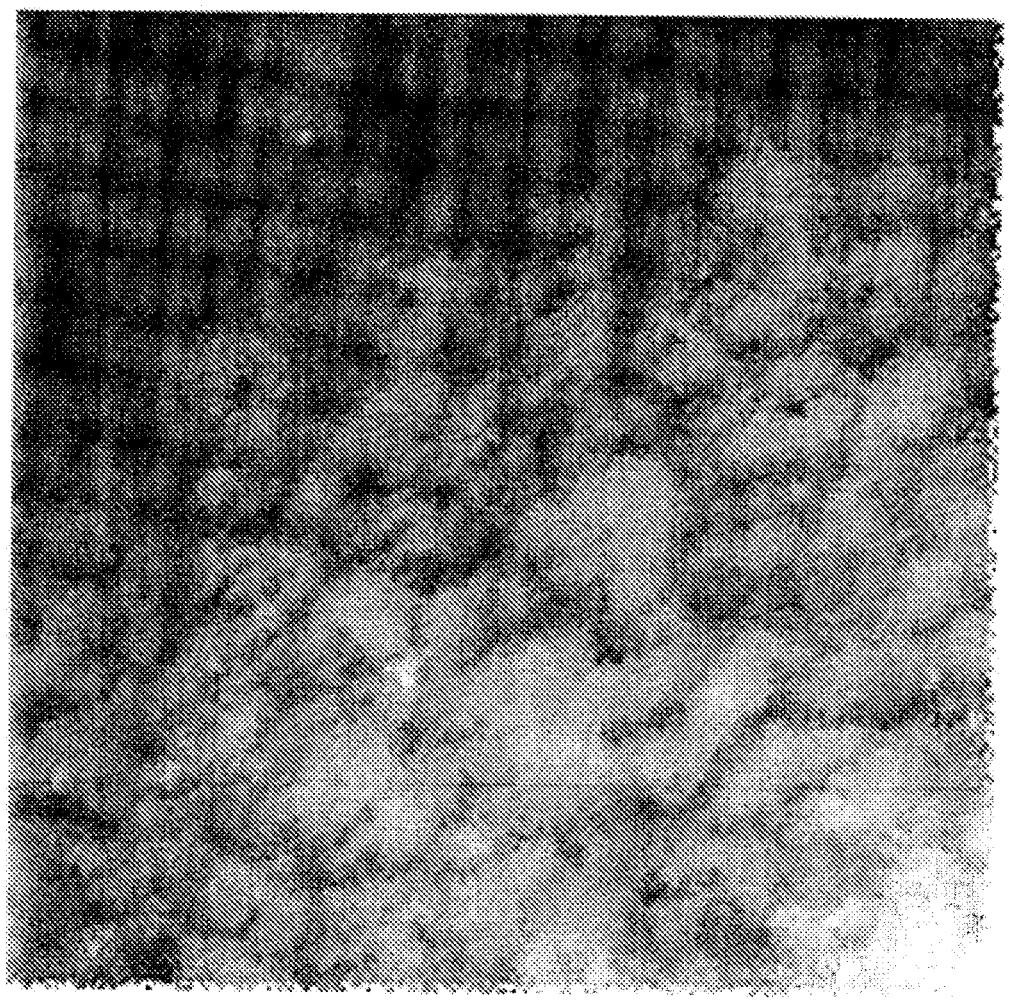
FIG. 7B This is an enlarged observation image of the inside of the lip observed by the endoscope device with a light quantity ratio set to 50:50.
Figure 7C:
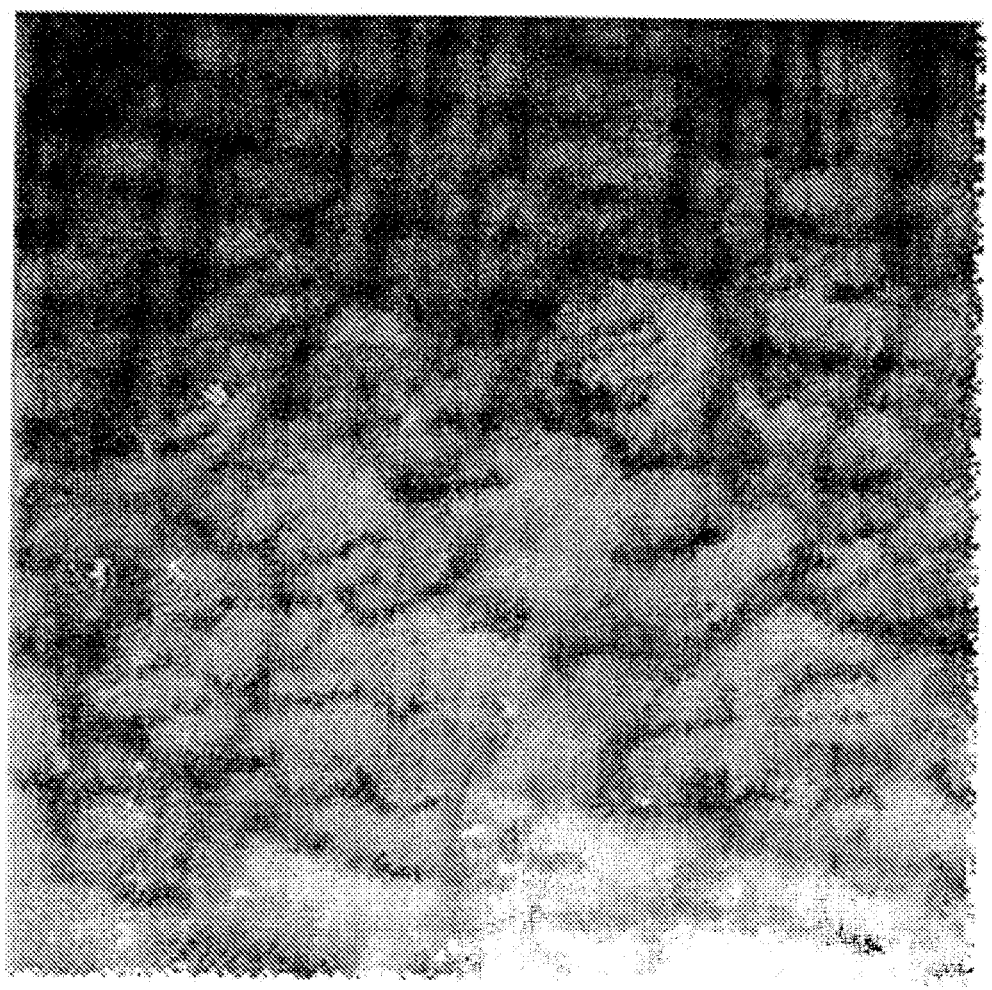
FIG. 7C This is an enlarged observation image of the inside of the lip observed with a light quantity ratio set to 75:25 by the endoscope device.

At this point, FIGS. 7A, 7B and 7C illustrate enlarged images of the inside of a lip observed by using the endoscope device 100 with the same light quantity under similar conditions of image processing. These drawings illustrate an observation image obtained with the white light illumination light including the blue laser beam of the center wavelength of 445 nm and the excited light of the phosphor (FIG. 7A), an observation image obtained when the light quantity ratio between the violet laser beam of the center wavelength of 405 nm and the blue laser beam of the center wavelength of 445 nm is set to 50:50 (FIG. 7B), and an observation image obtained when the light quantity ratio between the violet laser beam of the center wavelength of 405 nm and the blue laser beam of the center wavelength of 445 nm is set to 75:25 (FIG. 7C). It is noted that the excited light caused through the excitation of the blue laser beam of the center wavelength of 445 nm and emitted from the phosphor is included in the illumination light also in FIGS. 7B and 7C.

In the observation images of FIGS. 7A, 7B and 7C, the depth of the observation from the surface layer is smaller in the order of 7A, 7B and 7C in accordance with the wavelength of the illumination light, and the amount of minute blood capillaries shown is increased in this order. In other words, as the ratio of the violet laser beam in the illumination light is increased, the blood capillaries of the surface layer are more enhanced in the image, and hence, the blood capillaries of the mucosal surface layer and a mucosal fine pattern may be more clearly observed with increased contrast. Furthermore, since the light quantity ratio between the blue laser beam and the violet laser beam may be freely changed without stages, it is easy to presume a stereo structure of blood vessels in the mucosal surface layer or to selectively and clearly show a desired observation target on the basis of change in the observation image caused in continuously changing the light quantity ratio.

With regard to the violet light and the blue light of the wavelength bands close to each other, it is difficult to realize the increase/decrease of the light quantity of the violet region alone distinguishably from the light of the blue region by using a conventional halogen or xenon lamp and wavelength limiting means such as a color filter. When an emission spectrum is narrowed in the wavelength band by using the wavelength limiting means disposed on an optical path, the original light quantity of the halogen or xenon lamp is small, and in addition, the quantity of light of the violet region is further insufficient. Moreover, when the half-width of the emission spectrum is to be increased for increasing the quantity of the light of the violet region, the illumination light may not be narrowed in the wavelength band, and a desired blood vessel is insufficiently enhanced in a resultant image.

When the light quantity of the illumination light is insufficient, the insufficient light quantity may be dealt with generally by increasing the sensitivity of an image sensor or decreasing a frame rate, and however, when the sensitivity of the image sensor is increased in capturing an image, a noise component of the captured image is disadvantageously increased. Alternatively, when the sensitivity is increased by decreasing the frame rate, blurring is increased and an observation image becomes obscure on the contrary. Since the laser beams are used as the light sources in this exemplified structure, the illumination light with high intensity is always stably obtained, an observation image may be bright, and in addition, a high image quality with low noise may be obtained. Furthermore, even when an image of a distant site is captured, necessary sufficient luminous intensity may be attained.

The aforementioned light quantity ratio is changed by the light source control part 55 of FIG. 2 through control of the light sources 51 and 53, and next, a method for changing the light quantity ratio by an operator while keeping an observation image in sight will be described with reference to FIGS. 8 and 9.

Figure 8:
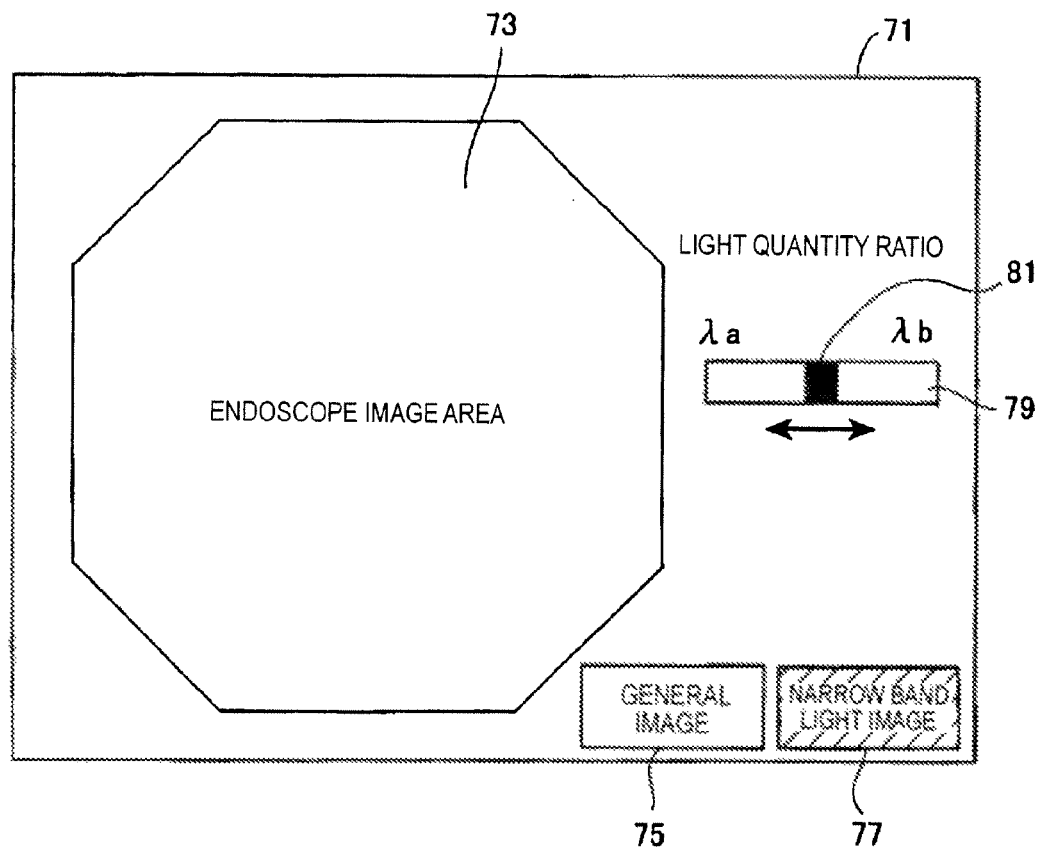
FIG. 8 This is an explanatory diagram illustrating an example of a display screen of a display part displaying an observation image obtained by the endoscope device.

FIG. 8 illustrates an example of a display screen 71 of the display part 15 for displaying an observation image obtained by the endoscope device 100. The display screen 71 is provided with an endoscope image area 73 where an observation image obtained by the endoscope device is displayed, a general image switching button 75 for allowing an observation image obtained with the general white light illumination to be displayed in the endoscope image area 73, and a narrow band light image switching button 77 for allowing an observation image obtained with narrow band illumination light of the violet laser beam to be displayed, and is further provided with an adjusting bar 79 and a knob 81 used for adjusting the light quantity ratio. On the basis of an instruction given through the input part 17 of a mouse or a keyboard, the knob 81 is slidingly moved inside the adjusting bar 79, so as to adjust the light quantity ratio for attaining a desired observation image.

The control part 67 determines the light quantity ratio in accordance with the position of the knob 81 in the adjusting bar 79, and drives the light sources 51 and 53 so as to attain the quantities of light emitted from the light sources 51 and 53 corresponding to the determined light quantity ratio. At this point, a relationship between the light quantity ratio and the quantities of light emitted from the light sources 51 and 53 is stored in a memory part 83 (see FIG. 2) as a light quantity ratio correspondence table, and the control part 67 obtains the quantities of light to be emitted from the light sources 51 and 53 by referring to the light quantity ratio correspondence table of the memory part 83.

In setting a desired light quantity ratio by increasing/decreasing the quantities of the light emitted from the light sources 51 and 53 (see FIG. 1) as described above, the control part 67 determines the quantities of the light to be emitted from the light sources 51 and 53 by referring to the light quantity ratio correspondence table precedently stored on the basis of the light quantity ratio set in the display screen 71. In this manner, a desired light quantity ratio may be obtained through a simple operation without an operator of the endoscope directly setting the quantities of the light to be emitted from the light sources 51 and 53.

Figure 9:
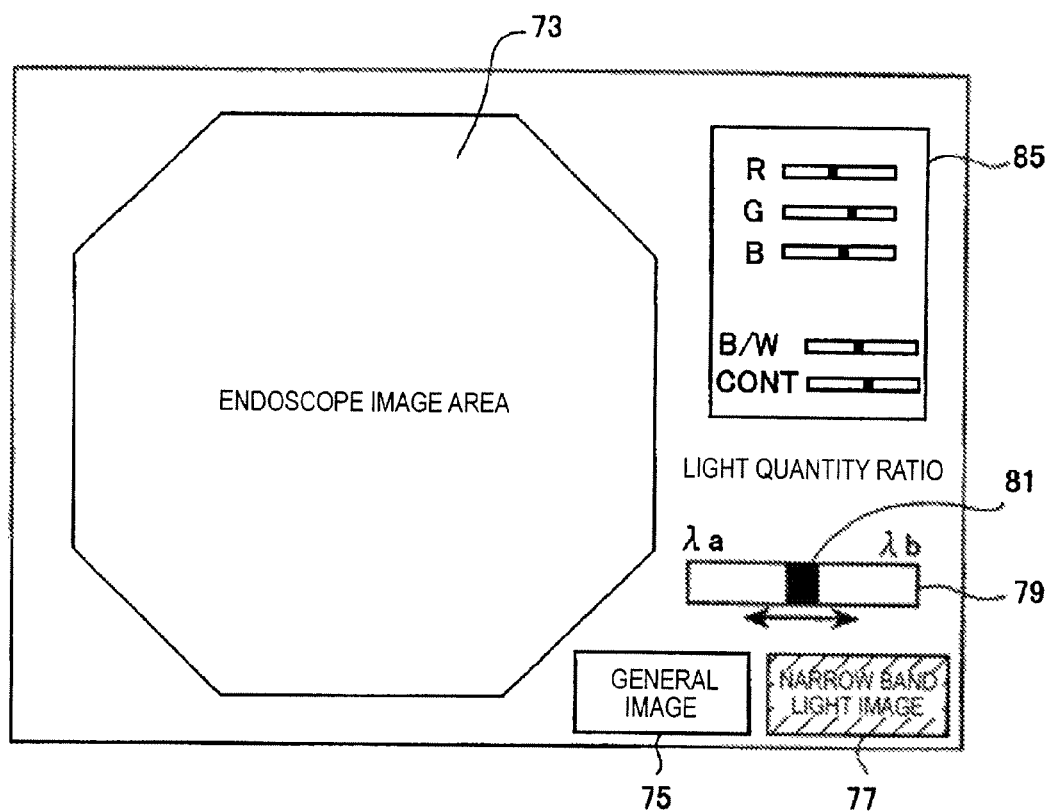
FIG. 9 This is an explanatory diagram illustrating another example of the display screen of the display part displaying an observation image obtained by the endoscope device.

Alternatively, as illustrated in FIG. 9, the light quantity ratio may be set instead by using a setting portion 85 for making various adjustments of intensity balance among the respective colors R, G and B of a picture signal, the brightness and the contrast, or by using the setting portion 85 in combination with the adjustment conducted by using the knob 81 for changing the light quantity ratio. In this manner, a desired observation target may be arbitrarily enhanced, for example, expressed in pseudo colors in an observation image, and thus, the degree of freedom in changing a displayed image may be increased, so as to obtain an image more suitable to diagnosis.

Next, a method for driving the light sources 51 and 53 by the light source control part 55 will be described.

Figure 10:
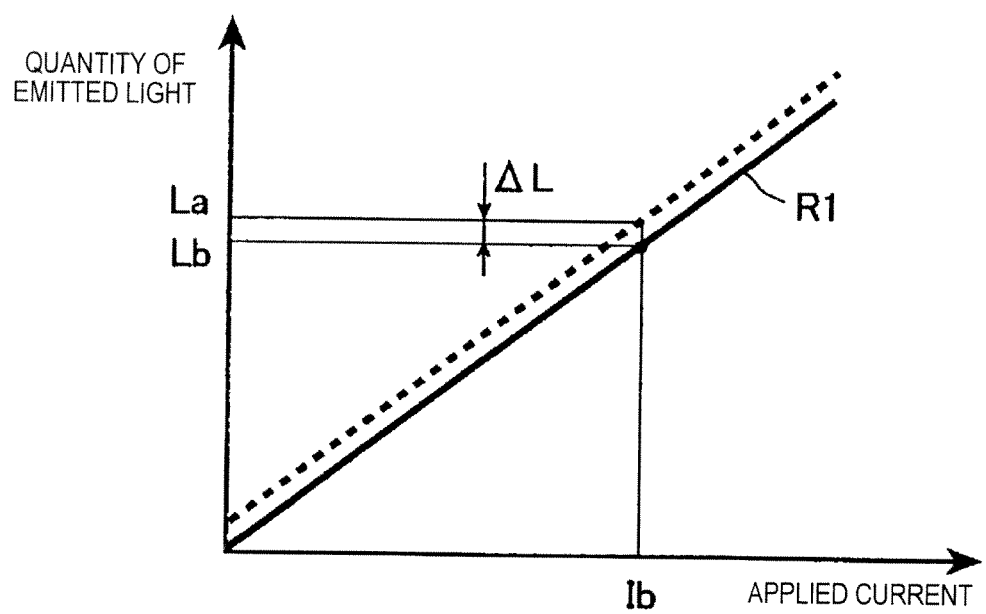
FIG. 10 This is a graph illustrating the relationship between a current applied to a light source and the quantity of emitted light.

The light source control part 55 of FIG. 2 controls the quantities of the light to be emitted from the light sources 51 and 53 on the basis of an instruction given through the input part 17. In each of the light sources 51 and 53, there is a relationship R1 between the applied current and the light quantity as illustrated in FIG. 10, and a desired light quantity may be attained by controlling the current applied to each of the light sources 51 and 53. In order to obtain a light quantity La, for example, the applied current is not to 1b for securing a light quantity Lb on the basis of the relationship R1, and a difference ΔL between the light quantity Lb and the light quantity La corresponding to a fine adjustment margin is obtained by superimposing, on the applied current, a pulse-modulated pulse current.

Figure 11:
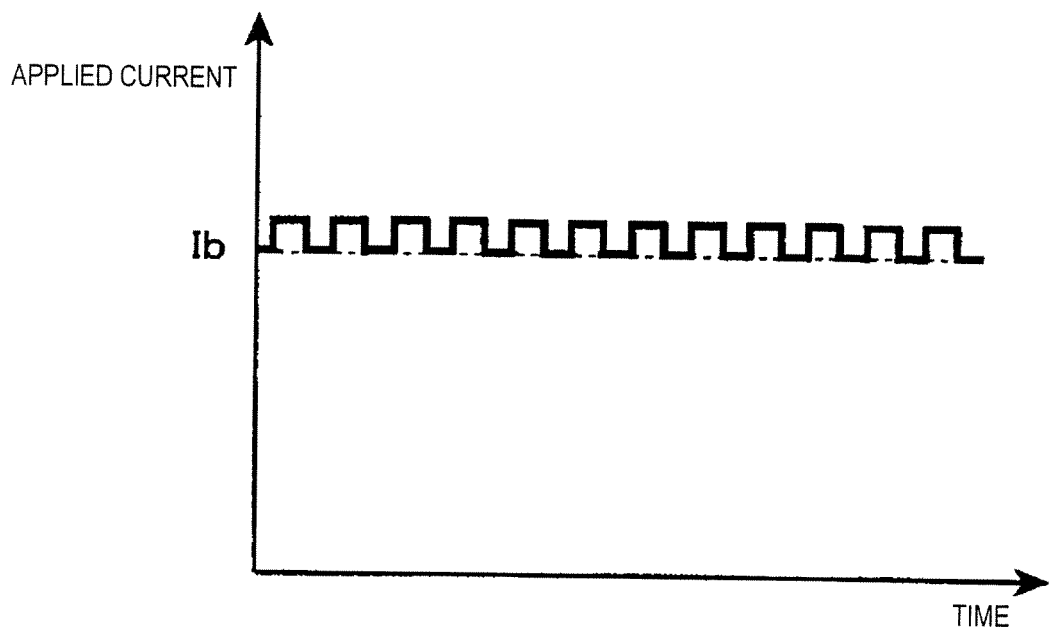
FIG. 11 This is a graph illustrating a pulse current superimposed waveform of the applied current.

For example, as understood from a pulse current superimposed waveform illustrated in FIG. 11, the light quantity La is obtained by a pulse current resulting from biasing the applied current Ib. Through such bias current control and pulse modulation control, a dynamic range of a settable light quantity may be widely secured.

Figure 12:
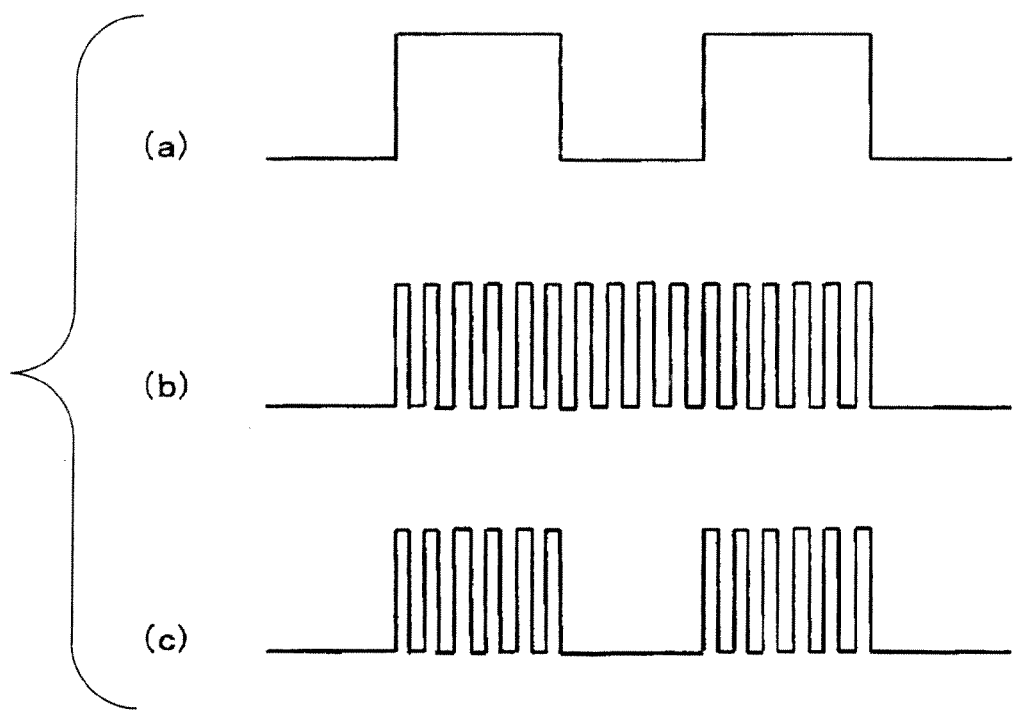
FIG. 12 This is an explanatory diagram illustrating various drive waveforms (a), (b) and (c) obtained under pulse modulation control.

For the pulse modulation control employed in this case, any of various drive waveforms may be used. For example, when a pulse waveform repeatedly turned on/off in synchronization with light storage time for one frame of an image of the imaging device as illustrated in FIG. 12(a) is used, it is minimally affected by a dark current of the CCD or CMOS image sensor, and hence, the fineness of a resultant image may be increased. Alternatively, when a pulse waveform with a cycle sufficiently faster than the light storage time as illustrated in FIG. 12(b) is used, the occurrence of flicker related to image display may be reduced, and in addition, image noise derived from speckle of the laser may be reduced. Alternatively, when a mixed type pulse waveform corresponding to a mixture of the pulse waveforms of FIGS. 12(a) and 12(b), specifically in which the fast cycle pulse waveform of FIG. 12(b) is employed in an on-period of the pulse waveform of FIG. 12(a), is used, the aforementioned effects other than the reduction of flicker may be attained.

Figure 13:
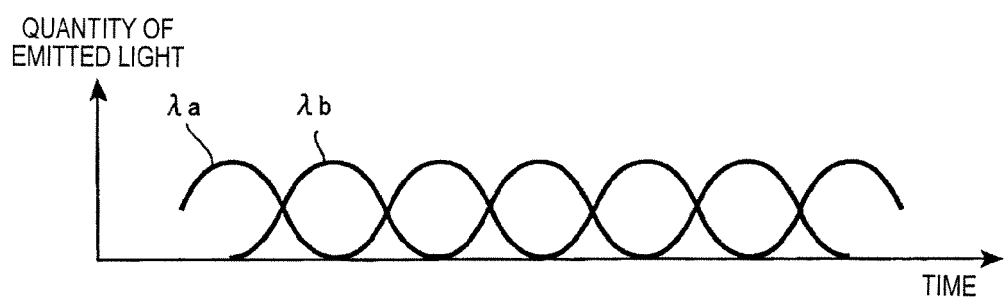
FIG. 13 This is a graph illustrating an example of control for alternately maximizing the quantities of light emitted from light sources.

Furthermore, when the light sources 51 and 53 are controlled to alternately turn on for alternately attaining the maximum light quantity as illustrated in FIG. 13, the maximum drive power of the light source system 41 for both the light sources 51 and 53 may be suppressed, and a burden on an organism, that is, a subject, may be reduced. Furthermore, captured images obtained with the illumination light of the light sources 51 and 53 may be individually obtained, and in this case, the captured images may be subjected to an inter-picture operation, and thus, the degree of freedom in the image processing may be increased.

Figure 14:
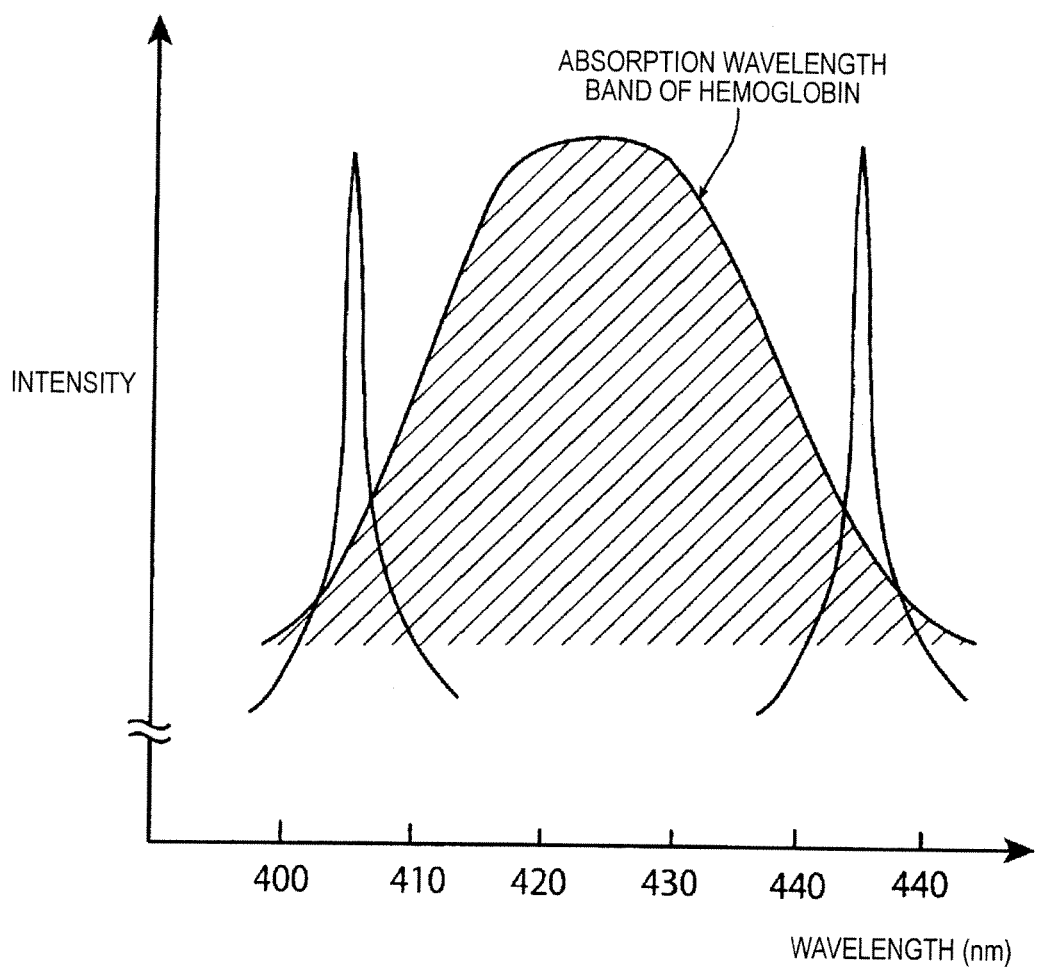
FIG. 14 This is a graph illustrating rough relationships between an absorption wavelength band of hemoglobin and emission wavelengths of the light sources.

FIG. 14 illustrates a rough relationship between absorption wavelength band of hemoglobin and the emission wavelengths of the light sources 51 and 53.

Hemoglobin included in blood has an absorption peak at a wavelength in the vicinity of 400 to 420 nm as described above, and hence, beams emitted from the light sources 51 and 53 and having emission wavelengths included in or in the vicinity of the absorption wavelength band of hemoglobin may capture blood vessel information with high contrast. Furthermore, since the emission wavelengths of the light sources 51 and 53 are set to have substantially the same absorption with the absorption wavelength band of hemoglobin sandwiched therebetween, intensity of the blood vessel information is never affected by the light quantity ratio between the light sources 51 and 53. In other words, even when the light quantity ratio between the light sources 51 and 53 is changed, the sensitivity in detecting a blood vessel image itself may be kept constant.

When light not having the maximum peak wavelength of the absorption wavelength band of hemoglobin and having appropriate absorption in base regions of the absorption wavelength band is used as the illumination light, even if organism tissue bleeds in an observation region, an observation image may be prevented from darkening by the influence of absorption by the blood having oozed out to the tissue surface layer.

Figure 15:
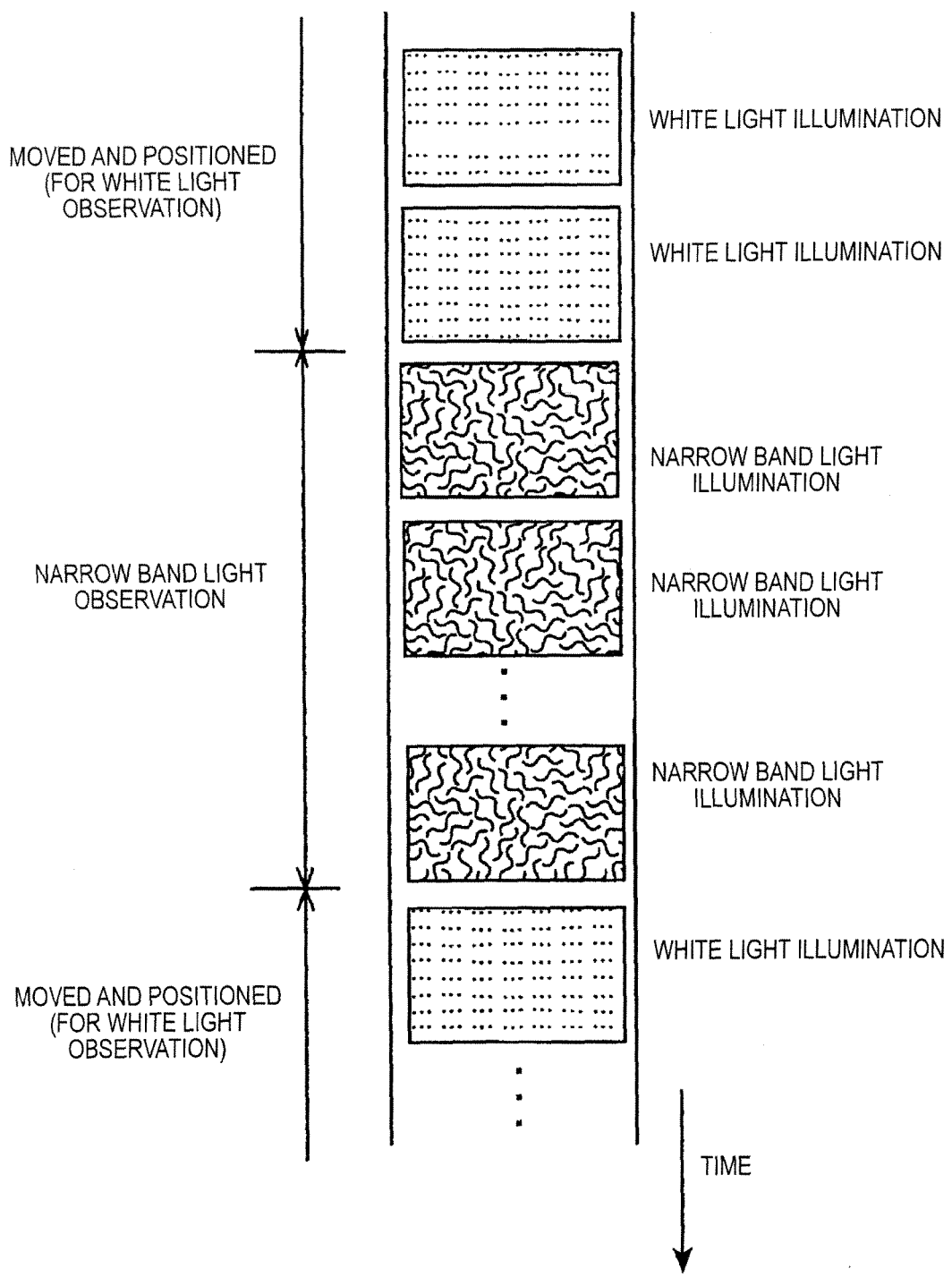
FIG. 15 This is an explanatory diagram schematically illustrating the states of a displayed image of the display part obtained when an operator of an endoscope moves the endoscope insertion section within a subject, performs observation in a desired observation position with narrow band light and moves it to a next observation position.

Observation images obtained by the illumination with the narrow band light of the violet laser beam and by the illumination with the white light described so far may be instantly switched with respect to every frame. FIG. 15 schematically illustrates states of displayed images of the display part 15 (see FIGS. 1 and 2) obtained when an operator of the endoscope moves the endoscope insertion section in a subject, performs the observation with the narrow band light in a desired observation position and moves the endoscope insertion section to a next observation position.

The switching from a general display image obtained through the white light observation to a display image obtained through the narrow band light observation and the reverse switching may be conducted with respect to each frame of a captured image (a full-color age of R, G and B colors) of the imaging device 21. Therefore, even when the observation is performed while moving the endoscope insertion section, images free from color drift may be displayed on a real-time basis, and hence, the operator can be prevented from feeling uncomfortable. In other words, good observation images that may definitely follow quick movement of the endoscope are provided, resulting in improving the operability of the endoscope device.

Figure 16:
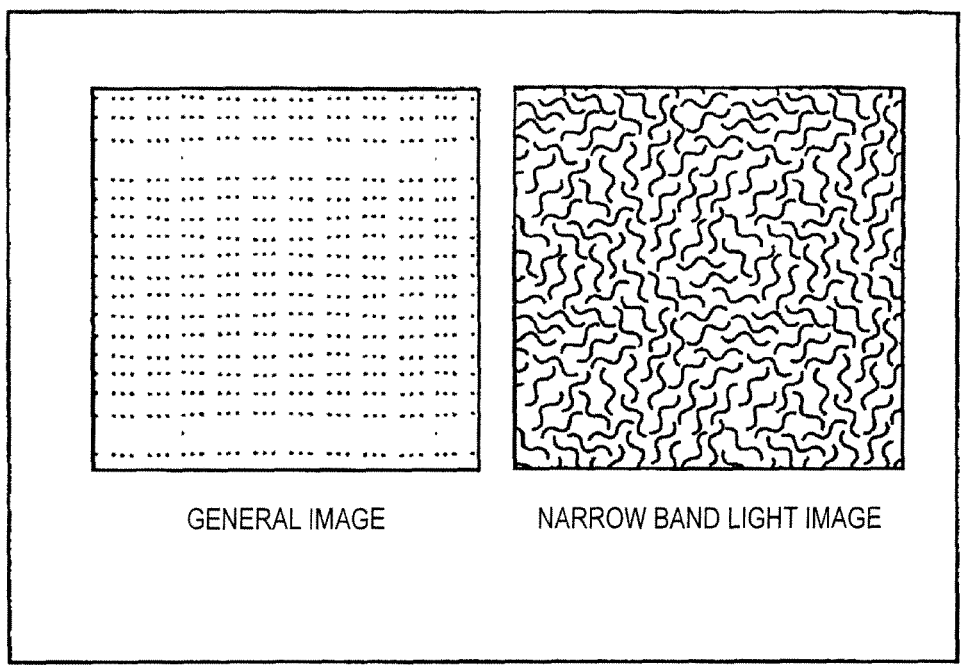
FIG. 16 This is an explanatory diagram illustrating an example in which a general image and a narrow band image are arranged in their individual positions within one screen to be simultaneously displayed.

Furthermore, as a display pattern for observation images in the display part 15, a general image obtained through the white light observation and a narrow band light image obtained through the narrow band light observation may be freely arranged. For example, when a general image and a narrow band light image are respectively arranged in individual areas in one screen to be simultaneously displayed as illustrated in FIG. 16, the general image and the narrow band light image in which specific information is enhanced may be easily compared with each other in the observation. In this case, image capture with the blue laser light source 51 turned on for a general image obtained with the white light and image capture for a next frame with the blue laser light source 51 and the violet laser light source 53 simultaneously turned on for a narrow band light image are repeated, and the thus obtained general images and narrow band light images are respectively displayed in their individual display areas.

Figure 17:
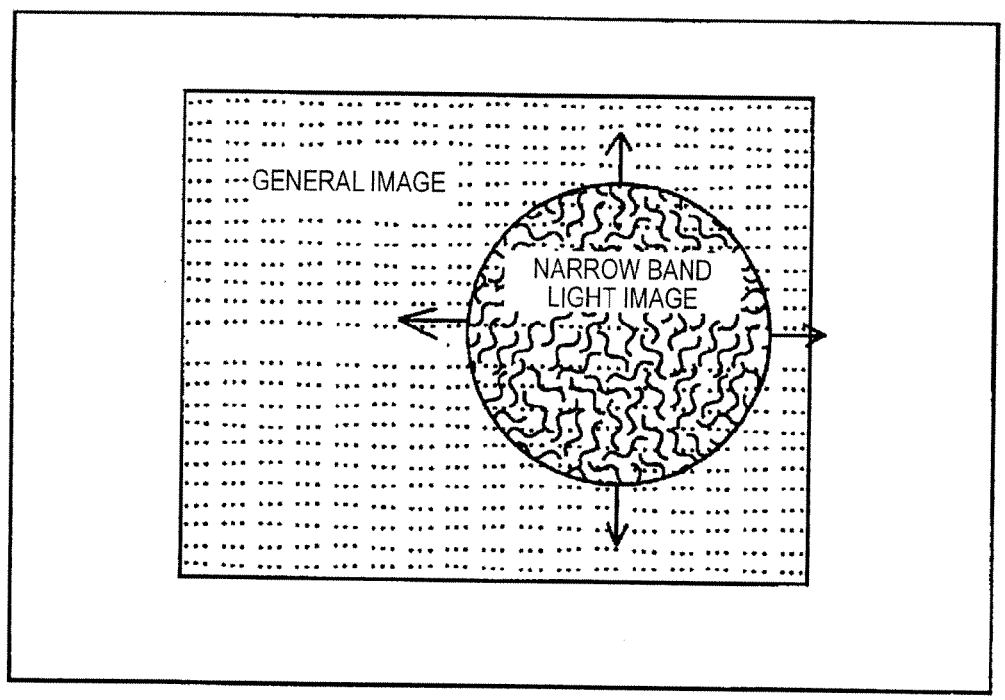
FIG. 17 This is an explanatory diagram illustrating an example in which a desired range of a narrow band image is overlapped on a general image to be simultaneously displayed.

Alternatively, FIG. 17 illustrates a display screen in which a desired range of a narrow band light image is overlapped on a part of a general image for simultaneous display, namely, a display screen having what is called a PinP (picture in picture) function. A display range of the narrow band light image may be set to an arbitrary position and in an arbitrary size in the general image in accordance with an instruction given through the input part 17 (see FIGS. 1 and 2). In the display range of the narrow band light image, a part of the narrow band light image of a subject in the same position as the corresponding part of the general image is displayed. In this manner, comparative observation of the images of the same position may be further easily conducted. Incidentally, the aforementioned display patterns are merely exemplarily described, a display form in which a general image is fit in a narrow band light image may be employed, and it goes without saying that any other possible combinations may be employed for the display.

Next, the setting of the light quantity ratio between the blue laser beam and the violet laser beam will be described.

As described above, the light quantity ratio between the light emitted from the blue laser light source 51 and the light emitted from the violet laser light source 53 of FIG. 2 may be arbitrarily set by the light source control part 55 in accordance with an instruction given trough the input part 17. Herein, description will be made on a case where plural kinds of light quantity ratios are precedently registered so as to specify one of the light quantity ratios by using the input part 17.

In the endoscope observation of images of, for example, blood vessels, operators of the endoscope may be different in their preference in the light quantity ratio between the blue laser beam and the violet laser beam. For example, an operator A may prefer an observation image obtained with the light quantity ratio between the violet laser beam λa and the blue laser beam λb set to 60:40 while an operator B prefers one obtained with the light quantity ratio set to 75:25, and thus, there may be a difference in the preference. In this case, as illustrated in FIG. 18, light quantity ratio information in which a name of an operator, that is, key information, is in relation to a light quantity ratio preferred by the operator, is precedently registered in the memory part 83 (see FIG. 2) or the like as a light quantity ratio table. Then, when information corresponding to a name of an operator is input through the input part 17, the control part 67 automatically sets a desired light quantity ratio by referring to the light quantity ratio table stored in the memory part 83. In this manner, a light quantity ratio may be set in accordance with the preference of an operator of the endoscope.

Furthermore, since optical characteristics may be sometimes different among individual endoscopes, individual identification information for identifying each of the individual endoscopes may be used as the key information instead of a name of an operator used as the key information above. In this case, a number, a model name or the like given to each of the endoscopes is used and information on a corresponding light quantity ratio is precedently registered as the light quantity ratio table. In this manner, an optimum light quantity ratio may be set in accordance with the type or the characteristics of each of the individual endoscopes.

Figure 19:
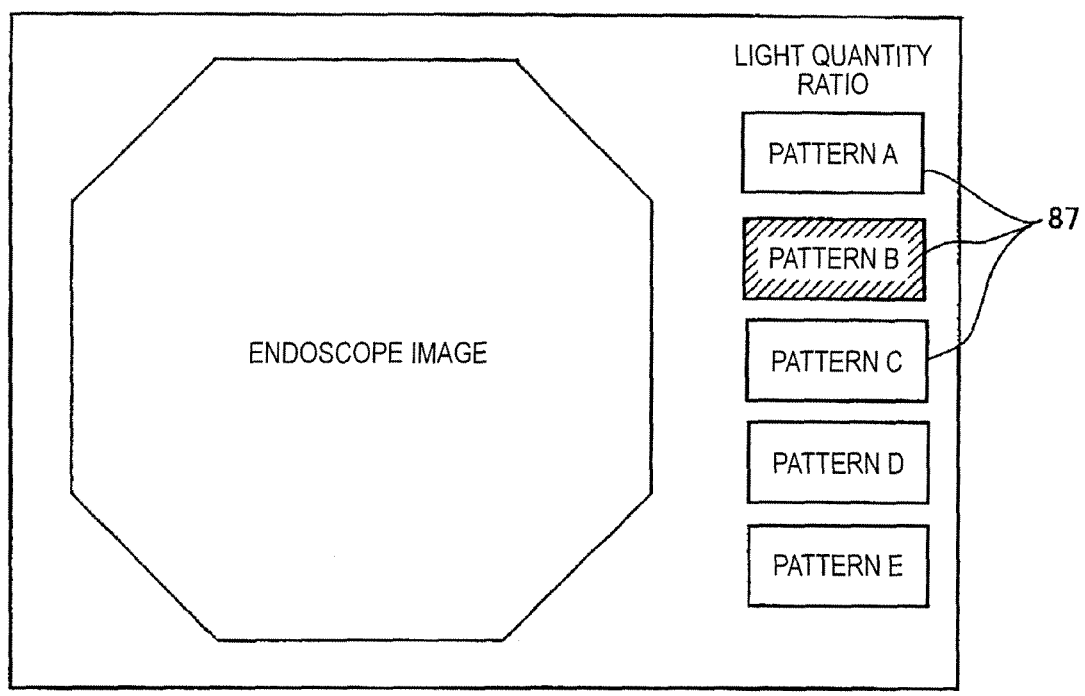
FIG. 19 This is an explanatory diagram illustrating an example in which preset light quantity ratios are displayed in the display part.

Moreover, arbitrary plural kinds of light quantity ratios may be preset so as to be freely selected through a simple operation performed by an operator. For example, as illustrated as a display example of the display part 15 in FIG. 19, plural kinds of preset light quantity ratios are displayed as "selection buttons" 87 of GUI (graphical user interface), which may be freely selected by an operator or an assistant by operating the input part 17 while seeing the display part 15 (see FIGS. 1 and 2). Furthermore, when the display part 15 is a touch panel, a switching operation may be more intuitively and quickly performed by directly touching one of the selection buttons 87 in the display part 15 steadily gazed by the operator during the observation. In addition, the operator may compare observation images changing in accordance with the change of the light quantity ratio without taking his/her eyes off, and hence, subtle change of the images may be more definitely recognized.

Furthermore, the switching of the light quantity ratio may be conducted not only by using the display pattern on the display part 15 but also by operating the switch 89 provided, as a change-over switch, on the operation section 23 of the endoscope 11 of FIG. 1. When the switch 89 is provided on the operation section 23, the light quantity ratio may be rapidly and easily changed without the operator releasing his/her grip on the endoscope 11, resulting in improving the operability of the endoscope.

Figure 20:
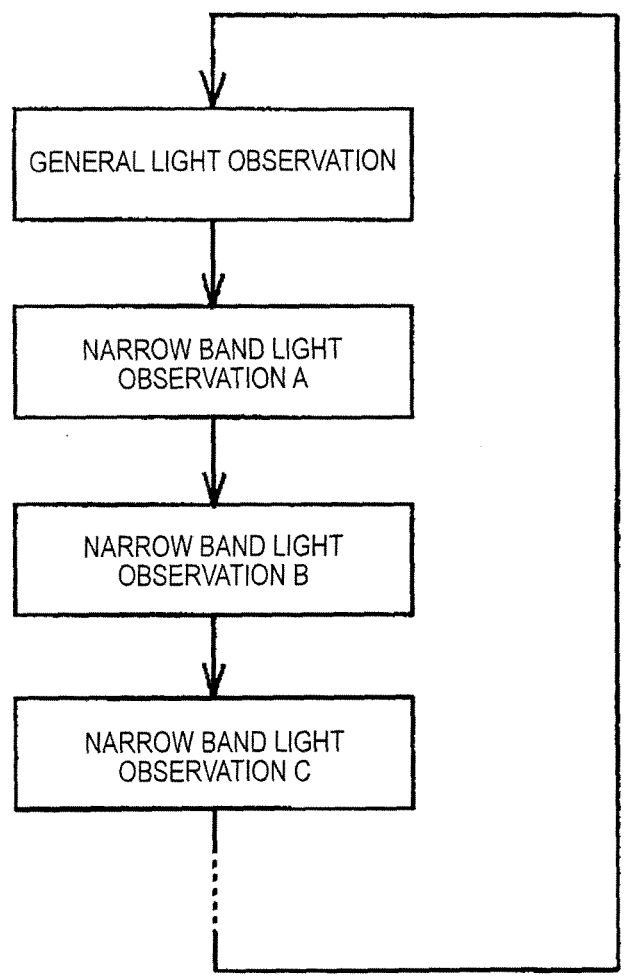
FIG. 20 This is an explanatory diagram of an operation of a change-over switch.

As the switch 89, any of various switches such as a toggle switch, a push switch, a slide switch and a rotary switch may be used, and as illustrated in FIG. 20, precedently preset different light quantity ratios are successively set every time the switch is pushed once or in accordance with a contact position of a multi-contact switch. Thus, it is possible to successively select observation light modes with plural kinds of light quantity ratios, such as the general light observation performed with the white light obtained by the blue laser light source 51 and the phosphor 57 of FIG. 2, narrow band light observations A, B, C, etc. in which the narrow band light emitted from the violet laser light source 53 is superimposed on the white light at prescribed ratios, and narrow band light observation performed with the narrow band light alone.

When the switching operation is performed through the repetition of a pushing operation, there is no need to visually recognize the switch 89 but the switching operation may be performed while gazing at the display part 15. Therefore, the illumination light suitable to diagnosis may be easily switched. Incidentally, the switch 89 for changing the light quantity ratio is not limited to a switch for changing the preset light quantity ratios but may be a volume switch or a slide switch for continuously changing the light quantity ratio. In this case, the light quantity ratio may be easily adjusted to be optimum in accordance with an observation target. Furthermore, when the light quantity ratio is continuously changed by the switching operation, continuous change of an observation image may be observed, and hence, a vascular structure may be more accurately grasped.

Next, correction of color change of an observation image caused by changing the light quantity ratio will be described.

The image processing part 65 of FIG. 4 receives picture signals R, G and B as inputs, and the picture signals R, G and B are normalized in the brightness by the brightness calculating section 65a, so as to be converted into image data Rnorm, Gnorm and Bnorm. These normalized image data Rnorm, Gnorm and Bnorm is subjected to correction to color tone according to the light quantity ratio by the color matching section 65b. Specifically, the color matching section 65b obtains image data Radj, Gadj and Badj resulting from the color tone correction through calculation in accordance with the following equation (1):

$$(R_{adj} G_{adj} B_{adj}) = (k_R k_G k_S) \begin{pmatrix} R_{norm} \\ G_{norm} \\ B_{norm} \end{pmatrix} \quad \text{Equation (1)}$$

In this equation, $k_R$, $k_G$ and $k_B$ respectively indicate color conversion factors of the respective colors and are determined in accordance with a light quantity ratio set in capturing the image. FIG. 21 illustrates a color conversion factor table in which the color conversion factors of the respective colors are listed correspondingly to light quantity ratios. The color conversion factors $k_R$, $k_G$ and $k_B$ are respectively set to R00 to R100, G00 to G100 and B00 to B100 correspondingly to the respective light quantity ratios, and are stored in the memory part 83 (see FIG. 2). When the color conversion factors corresponding to a light quantity ratio employed in capturing an image are substituted in Equation (1), image data Radj, Gadj and Badj resulting from the color tone correction is obtained.

The color conversion factors may be expressed not only as the table of FIG. 21 but also as an equation, or alternatively, with merely representative points digitalized, other points may be calculated through an interpolation operation. In this case, the amount of information stored in the memory part 83 may be reduced.

According to the endoscope device 100 described so far, since the violet laser beam (and the blue laser beam), namely, the illumination light of a shorter wavelength band suitable to the observation of blood vessels in particular, is used, minute blood vessels of organism tissue surface layer may be enhanced in an image to be observed, and hence, the microstructure of the blood vessels may be easily observed. Furthermore, since the light quantity ratio between the violet laser beam and the blue laser beam (white light) may be continuously changed, a vascular structure changing along the depth direction from the organism tissue surface layer may be easily observed, and hence, the vascular structure in a shallower surface layer portion of the organism tissue may be clearly grasped. Therefore, in the observation of the organism tissue with the white light or special light, desired tissue information on the organism tissue may be obtained in a clearer state suitable to diagnosis, and thus, the endoscopic diagnosis may be smoothly performed.

Furthermore, when the endoscope device 100 employs a structure of what is called a magnifying endoscope including an imaging optical system capable of enlarging an observation target region for observation, separation between minute blood vessels of organism tissue surface layer and a mucosal fine pattern may be increased, and the endoscopic diagnosis may be performed at a higher level. Specifically, occurrence of unusual change such as a difference in the diameter or the shape among microvessels, and expansion and meandering thereof, and unusual change such as disappearance or abnormal size reduction of a mucosal fine pattern may be found, and hence, useful information for, for example, diagnosing the type of adenocarcinoma may be provided.

Next, an alternative structure of the endoscope device will be described.

First, an endoscope device that obtains an oxygen concentration distribution in blood in an observation image by utilizing a difference in the absorption characteristic between hemoglobin and oxygenated hemoglobin will be described.

Figure 22:
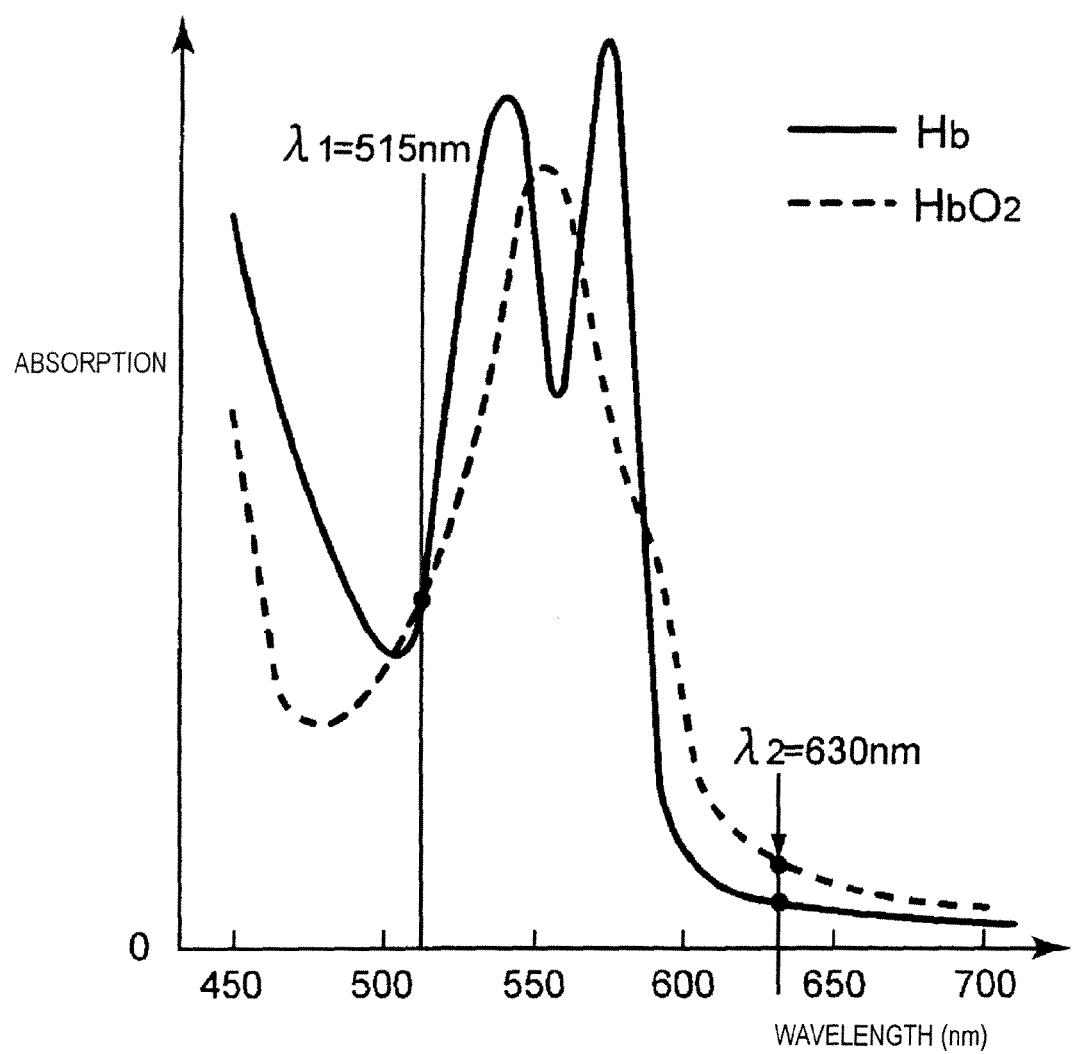
FIG. 22 This is a graph illustrating absorption spectra of hemoglobin Hb with a low oxygen concentration and oxygenated hemoglobin $HbO_2$ saturated with oxygen.

FIG. 22 illustrates absorption spectra, at a wavelength of 450 nm to 700 nm, of hemoglobin Hb with a low oxygen concentration and oxygenated hemoglobin $HbO_2$ saturated with oxygen. As the illumination light for the observation, a wavelength $\lambda 1$ corresponding to an isosbestic point where hemoglobin Hb and oxygenated hemoglobin HbO2 have the same absorption and a wavelength $\lambda 2$ where they have different absorption are selected, and brightness Ab1 of an observation image obtained with the illumination light of the wavelength $\lambda 1$ and brightness Ab2 of an observation image obtained with the illumination light of the wavelength $\lambda 2$ are obtained.

A ratio between the brightness Ab1 and Ab2 of these images is used as an index corresponding to an oxygen concentration in blood, and change in the metabolism state of organism tissue may be monitored by using this index. It is said in general that the oxygen concentration is low in a cancer region, and the oxygen concentration is useful information for the endoscopic diagnosis.

Figure 23:
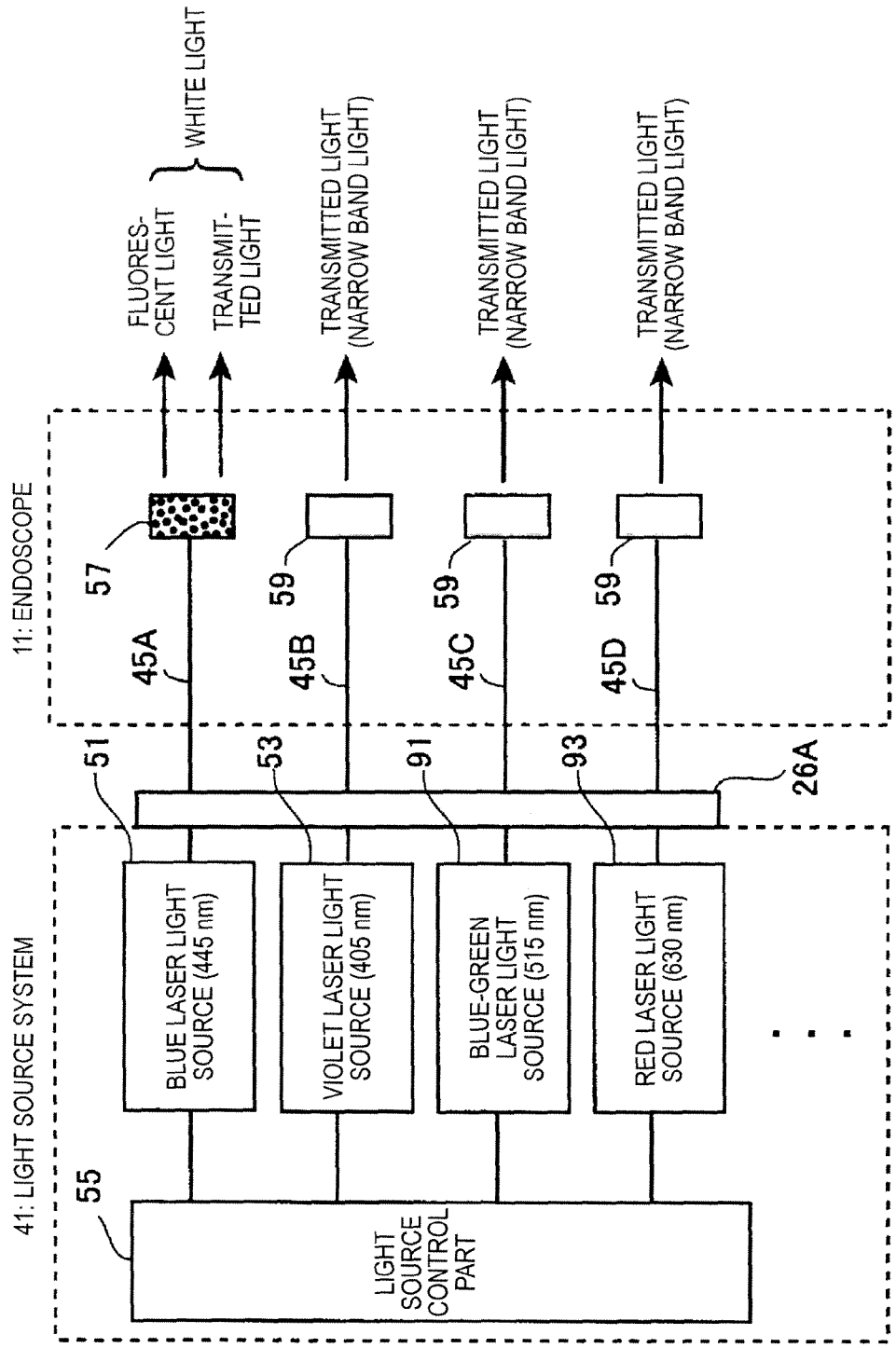
FIG. 23 This is a block diagram illustrating an exemplified structure of a light source system including a plurality of laser light sources and an endoscope.

As a structure of an endoscope device for obtaining the aforementioned oxygen concentration distribution, an endoscope device 200 additionally includes a plurality of light sources in a light source system 41 as illustrated as an exemplary structure of the light source system 41 and an endoscope 11 in FIG. 23. In this case, a blue-green laser beam emitted from a blue-green laser light source 91 with a center wavelength of 515 nm is used as the illumination light corresponding to the isosbestic point, for example, and a red laser beam emitted from a red laser light source 93 with a center wavelength of 630 nm is used as the illumination light corresponding to the wavelength where the absorption is different. Needless to say, in the case where the measurement of the oxygen concentration distribution is a main object, a violet laser light source 53 may be omitted. It is noted that like reference numerals are used in this drawing to refer to like elements used in FIG. 2 so as to omit the description.

Incidentally, optical fibers 45A, 45B, 45C and 45D used in the aforementioned structure are preferably selected to be optimum respectively for wavelengths to be employed. A core of an optical fiber has wavelength dependency in which transmission loss is varied in accordance with the concentration of hydroxyl groups (OH$^-$), and an absorption ratio attained at a specified wavelength of the infrared region is different from one attained at a wavelength of the visible range. Therefore, when the wavelength of a light source is 650 nm or less, an optical fiber using a core with a high hydroxyl concentration is used, and when the wavelength exceeds 650 nm, an optical fiber using a core with a low hydroxyl concentration is used.

In order to obtain the oxygen concentration distribution, an image of an observation target region is captured by using the blue-green laser beam emitted from the blue-green laser light source 91 as the illumination light, and then, an image of the observation target region is captured by using the red laser beam emitted from the red laser light source 93 as the illumination light. In capturing the images, the quantities of light emitted from the light sources 91 and 93 are respectively adjusted so as to make constant an average brightness value of observation image data. Thereafter, on the basis of brightness Ab1 and Ab2 of the thus obtained observation images, an oxygen concentration index Oindx is obtained with respect to each pixel in accordance with the following Equation (2):

$$Oindx = k \cdot (Ab2/Ab1) \quad \text{Equation (2)}$$

wherein k is a coefficient.

In this manner, an image of a distribution of the oxygen concentration index Oindx is obtained, and a distribution state of the oxygen concentration in the observation image may be grasped.

Furthermore, the blue-green laser light source 91 and the red laser light source 93 may be individually changed in the quantity of light emitted therefrom by a light source control part 55 similarly to the blue laser light source 51 and the violet laser light source 53, and the light quantity ratio between the light emitted therefrom may be adjusted in accordance with an observation target or the content of manipulation. Furthermore, each of the laser light sources 91 and 93 may be allowed to emit light in every frame of an imaging signal so as to appropriately adjust the light quantity ratio therebetween. The blue-green laser beam is suitably used for observation of microvessels or flare of organism tissue, and the red laser beam is suitably used for observation of deep vessels of organism tissue. Accordingly, when the light quantity ratio between these emitted laser beams is changed, information from regions different along the depth direction or information from different targets may be enhanced in images to be displayed in the same manner as described above.

Moreover, even when the light sources are allowed to simultaneously emit light in one frame of an imaging signal, a light component derived from the blue-green laser light source 91, a light component derived from the red laser light source 93 or a quantity of excited light may be separately detected from R, G and B picture signals output from the imaging device 21.

In this manner, when the light quantity ratio of the blue-green laser beam to the white light, the light quantity ratio of the red laser beam to the white light or the light quantity ratio between the blue-green laser beam and the red laser beam may be arbitrarily and continuously changed, visibility of a desired observation target may be improved for display. Therefore, when the number of kinds of illumination light of an endoscope is increased to attain multiple functions, even if there arises unexpected necessity of observation during endoscopic diagnosis, the observation may be promptly conducted with illumination light appropriate to an observation target without evulsing the endoscope from the subject. Incidentally, instead of generating the white light from the blue laser beam and the excited light of the phosphor, a structure using a white light source such as a halogen lamp may be employed. In this case, the light quantity of the blue laser beam and the light quantity of the white light may be individually controlled, and hence, the light quantity ratio may be more finely adjusted.

Next, an endoscope device in which an optical path from a light source system 41 up to an endoscope 11 is constructed by one optical fiber 45 will be described.

Figure 24:
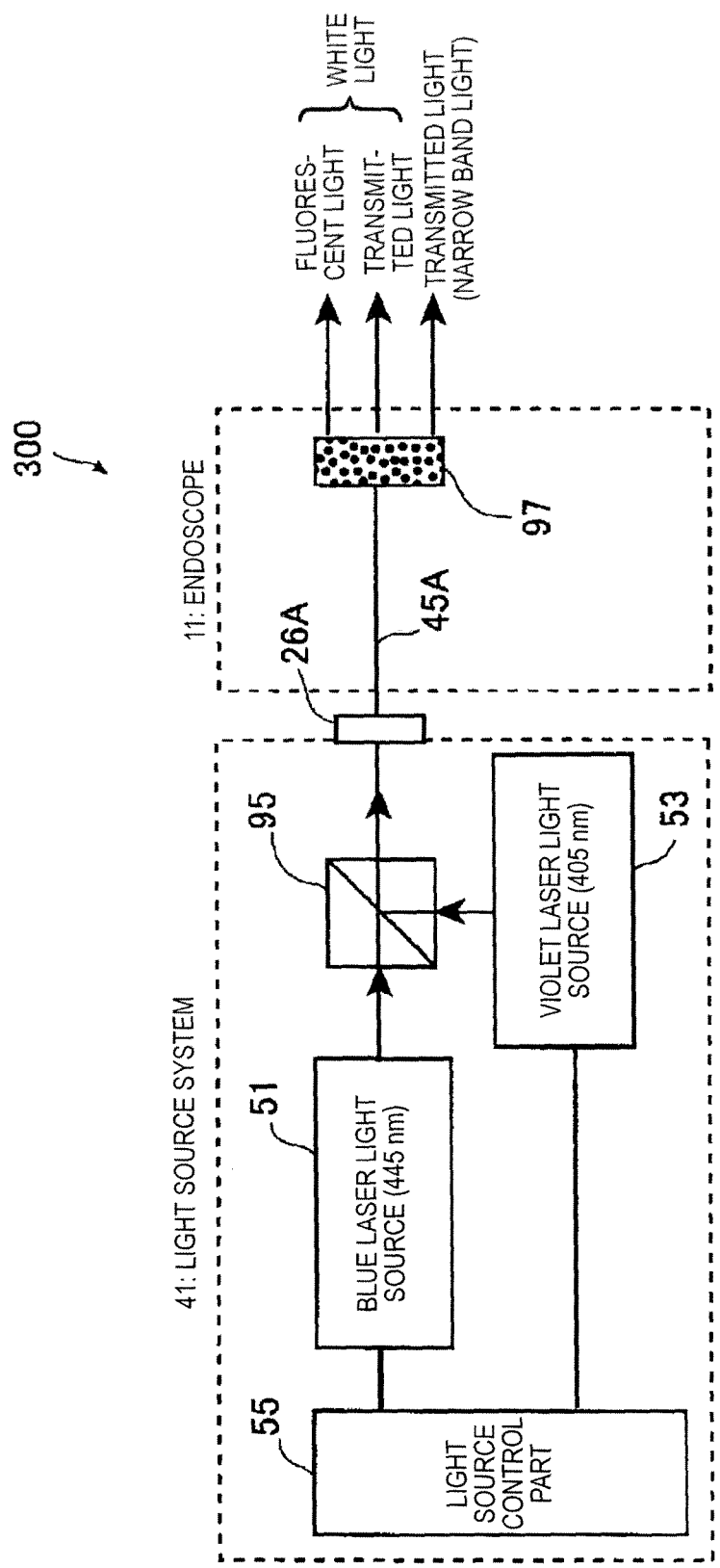
FIG. 24 This is a block diagram illustrating an exemplified structure of a light source system including an integrated optical path and an endoscope.

FIG. 24 illustrates an exemplified structure of the light source system 41 and the endoscope 11. This endoscope device 300 includes, on an optical path where a blue laser beam emitted from a blue laser light source 51 with a center wavelength of 445 nm is introduced through a condensing lens not shown to an optical fiber 45A, a dichroic prism 95 corresponding to optical coupling means for merging a violet laser beam emitted from a violet laser light source 53 with a center wavelength of 405 nm.

A phosphor 97 disposed on a light emitting side of the optical fiber 45A has characteristics to absorb a part of the blue laser beam emitted from the blue laser light source 51 so as to cause excitation emission of green to yellow light and generate white light by combining the excited light with the blue laser beam not absorbed by but having passed through the phosphor, and a characteristic to minimally absorb but transmit the violet laser beam emitted from the violet laser light source 53. Therefore, a material that generates white light by combining excited light caused at high efficiency by a blue laser beam with the blue laser beam and a material that causes minimum light emission of the phosphor by a violet laser beam are selectively used for the phosphor 97.

There is wavelength conversion loss (Stokes loss) such as heat generation principally caused in the wavelength conversion attained by the phosphor 97. Therefore, it is known that the efficiency in light emission of the phosphor is higher and the heat generation of the phosphor may be advantageously suppressed when an excitation wavelength with a longer emission wavelength is selected. Therefore, in the exemplified structure, a laser beam of a longer wavelength is used for generating the white light, so as to improve the light emission efficiency.

Figure 25:
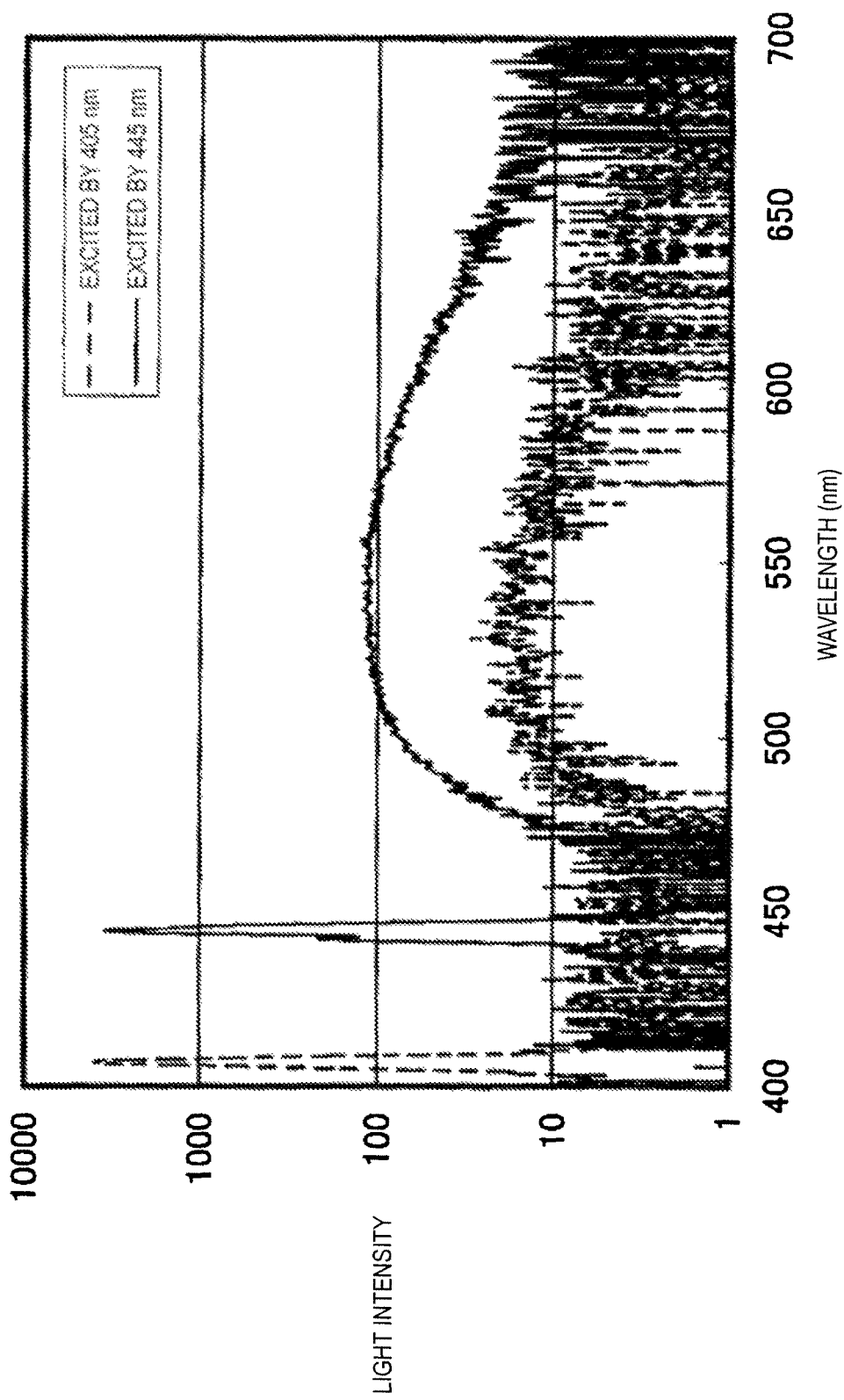
FIG. 25 This is a graph illustrating emission spectra of the light source system and a phosphor of FIG. 24.

FIG. 25 illustrates exemplified emission spectra of the illumination light obtained by the light source system 41 and the phosphor 97 of FIG. 24. As illustrated in FIG. 25, the quantity of excitation emission of the phosphor 97 caused by the violet laser beam is preferably one-severalth (at least one-third, preferably one-fifth and more preferably one-tenth or less) as compared with the quantity of light emission caused by the blue laser beam.

In this manner, since the dichroic prism 95 is used for integrating the optical path of the blue laser beam with that of the violet laser beam in this exemplified structure, merely one optical fiber 45A is used for guiding the light from the light source system 41 up to the phosphor 97, and in addition, since an outgoing port for the illumination light may be disposed in one position of the phosphor 97, the space efficiency may be improved so as to make a contribution to diameter reduction of an endoscope insertion section.

Furthermore, also when an alternative laser light source is included apart from the blue laser light source 51 and the violet laser light source 53, optical coupling means such as a dichroic prism may be similarly used for integrating optical paths. Also, with respect to the phosphor 97, a fluorescent material not excited or minimally excited by a wavelength of the alternative laser light source may be used.

At this point, as a specific material for the phosphor 97 used in this exemplified structure, for example, a solid crystalline fluorescent material including lead (Pd) as an additional element and digallium calcium tetrasulfide ($CaGa_2S_4$) as a parent body as described in Japanese Laid-Open Patent Publication No. 2006-2115-A, or a solid crystalline fluorescent material including lead (Pd) and cerium (Ce) as additional elements and digallium calcium tetrasulfide ($CaGa_2S_4$) as a parent body may be used. When such a fluorescent material is used, phosphor covering substantially the whole visible range of approximately 460 nm to 660 nm may be obtained, and thus, color rendering properties attained in the illumination with the white light may be improved.

Alternatively, a green phosphor of $LiTbW_2O_8$ (see "Phosphor for White Light Emitting Diode" by Tsutomu Odaki, The Institute of Electronics, Information and Communication Engineers Technical Report ED2005-28, CFM005-20, SDM2005-28, pp. 69-74 (2005-05), etc.), a β-sialon:Eu blue phosphor (see "New Sialon Phosphors and White LEDs" by Naoto Hirosaki, Rong-Jun Xie, Ken Sakuma, Oyo Buturi, Vol. 74, No. 11, pp. 1449-1452 (2005) or Hajime Yamamoto, Tokyo University of Technology, Bionics Department, Oyo Buturi, Vo. 76, No. 3, p. 241 (2007)), a $CaAlSiN_3$ red phosphor and the like may be combined for use. The β-sialon is crystal obtained by solid solving aluminum and an acid in β-silicon nitride crystal and represented by a composition of $Si_{6-z}Al_zO_zN_{8-z}$ (wherein z is a solid solution amount). The phosphor 97 may be a mixture of $LiTbW_2O_8$, β-sialon and $CaAlSiN_3$, or may be made of a layered structure of these phosphors.

Each of the phosphors exemplarily mentioned above is set to be excited by the blue laser beam emitted from the blue laser light source 51 but not to be excited to emit light by the violet laser beam emitted from the other violet laser light source 53, namely, is set to have a principal excitation wavelength band peculiar to the phosphor not including the emission wavelength of the other light source.

Although the white light is generated by using the blue laser beam and the excited light emitted from the phosphor 57 or 97 in the aforementioned endoscope devices, this does not limit the invention, but the white light may be generated by combining any of various light sources and phosphors, for example, by a structure using a phosphor excited to emit green light by a blue laser beam and a phosphor excited to emit red light by a violet laser beam.

As described so far, the followings are herein disclosed:

(1) A lighting device for an endoscope obtaining illumination light by using light emitted from a plurality of light sources, including: a first light source that uses a semiconductor light emitting device as an emission source; a second light source that uses, as an emission source, another semiconductor light emitting device of a different emission wavelength from the first light source; a wavelength converting member that is excited for light emission by light emitted from at least one of the first and second light sources; and light quantity ratio changing means that changes a light quantity ratio between the light emitted from the first light source and the light emitted from the second light source.

According to this lighting device for an endoscope, since the light quantity ratio between the light emitted from the first light source and the light emitted from the second light source may be freely changed, illumination light including a light component emitted from the first light source in a larger ratio, illumination light including a light component emitted from the second light source in a larger ratio and illumination light halfway therebetween may be arbitrarily generated. Accordingly, illumination light suitable to diagnosis may be provided in accordance with the absorption characteristic and the scattering characteristic of organism tissue, and hence, desired tissue information of the organism tissue may be obtained in a clearer state.

(2) In the lighting device for an endoscope according to (1), the semiconductor light emitting device of at least one of the first light source and the second light source has an emission wavelength of 400 nm to 470 nm.

According to this lighting device for an endoscope, since light of the semiconductor light emitting device of a wavelength of 400 nm to 470 nm is used, blood vessels of a surface layer portion of organism tissue may be particularly enhanced for observation.

(3) In the lighting device for an endoscope according to (1) or (2), the wavelength converting member is a phosphor for generating white light by using light emitted from the wavelength converting member by excitation light and the light emitted from at least one of the first and second light sources.

According to this lighting device for an endoscope, since the white light is generated by using the light emitted by the wavelength converting member with the light from the semiconductor light emitting device used as excitation light, white light with high intensity may be obtained at high efficiency. Furthermore, since the semiconductor light emitting device is used as the excitation light source, the intensity of the white light may be easily adjusted, and in addition, change in color temperature and chromaticity of the white light may be small.

(4) The lighting device for an endoscope according to any of (1) to (3), further including: at least one third light source that uses, as an emission source, a semiconductor light emitting device of a different emission wavelength from the first and second light sources, with the emission wavelengths being different among the light sources.

According to this lighting device for an endoscope, since it further includes the third light source having the different emission wavelength, the wavelength band of the illumination light may be increased, and the degree of freedom in selecting the wavelength of the illumination light may be improved. Therefore, illumination light for forming various images, such as a blood vessel enhanced image obtained with violet light or blue light and an oxygen concentration distribution image obtained with green light and red light, may be obtained.

(5) The lighting device for an endoscope according to any of (1) to (4), further including: optical coupling means that is disposed on an optical path extending from the first light source to the wavelength converting member and that guides the light emitted from at least the second light source together with the light emitted from the first light source to the wavelength converting member.

According to this lighting device for an endoscope, a portion extending from the optical coupling member to the wavelength converting member may be constructed by an optical path of one system, and hence, in fitting the lighting device for an endoscope in an endoscope device, a simple structure with improved space efficiency may be attained.

(6) In the lighting device for an endoscope according to any of (2) to (5), the emission wavelength of one of the first light source and the second light source is set to a wavelength on a shorter wavelength side and the emission wavelength of the other is set to a wavelength on a longer wavelength side of a maximum peak wavelength of an absorption wavelength band of hemoglobin sandwiched therebetween.

According to this lighting device for an endoscope, blood vessel information may be captured with high contrast. Furthermore, since the illumination light minimally includes a component in the vicinity of a peak of the absorption wavelength of hemoglobin, an observation image may be prevented from darkening through absorption of blood oozed out to a tissue surface layer.

(7) In the lighting device for an endoscope according to any of (1) to (6), the light quantity ratio changing means changes quantities of the light emitted from the light sources independently.

According to this lighting device for an endoscope, since the light quantity of light emitted from each of the light sources may be freely changed, the spectral characteristics of the illumination light ultimately generated from the light of the respective light sources may be adjusted at a high degree of freedom.

(8) The lighting device for an endoscope according to any of (1) to (7), further including: input means that is input light quantity ratio information specifying a desired light quantity ratio, the light quantity ratio changing means respectively determining the quantities of the light emitted from the light sources for attaining the desired light quantity ratio based on the light quantity ratio information input to the input means.

According to this lighting device for an endoscope, the light quantity ratio is specified in accordance with the light quantity ratio information input through the input means, and the quantities of the light emitted from the light sources are determined so as to attain the light quantity ratio. In other words, the light quantity ratio may be freely changed as specified.

(9) The lighting device for an endoscope according to (8), further including: memory means that stores a light quantity ratio table listing key information in relation to a plurality of light quantity ratios, the light quantity ratio information including the key information, the light quantity ratio changing means determining the desired light quantity ratio by referring to the light quantity ratio table based on the key information included in the light quantity ratio information input through the input means.

According to this lighting device for an endoscope, the desired light quantity ratio is determined by referring to the light quantity ratio table on the basis of the key information included in the light quantity ratio information. In other words, since the light quantity ratios are precedently registered in relation to respective key information in the light quantity ratio table, the light quantity ratio corresponding to key information may be automatically determined merely by specifying the key information.

(10) In the lighting device for an endoscope according to (9), the key information is identification information of an operator of an endoscope device.

According to this lighting device for an endoscope, an arbitrary light quantity ratio may be set with respect to each operator of the endoscope in accordance with preference of the operator.

(11) In the lighting device for an endoscope according to (9), the key information is individual identification information of an endoscope device.

According to this lighting device for an endoscope, the light quantity ratio may be set with respect to each individual endoscope in accordance with the type and the characteristic of the individual endoscope.

(12) In the lighting device for an endoscope according to any of (9) to (11), the input means is a change-over switch for specifying any of the plurality of light quantity ratios listed in the light quantity ratio table.

According to this lighting device for an endoscope, a desired light quantity ratio may be arbitrarily specified out of a plurality of kinds of light quantity ratios by operating the change-over switch, and thus, the light quantity ratio may be rapidly and easily switched.

(13) An endoscope device, including: illuminating means that emits the illumination light obtained by the lighting device for an endoscope of any one of (1) to (12) from a tip portion of an endoscope insertion section to be inserted into a body cavity; and imaging means that includes, in the endoscope insertion section, an imaging device for capturing an image of an observation target region irradiated with the illumination light and that outputs a picture signal for forming an observation image.

According to this endoscope device, the illumination light obtained with the light quantity ratio between the light emitted from the first light source and the light emitted from the second light source set to a desired light quantity ratio is used for irradiating an observation target region and an image of the observation target region is captured by the imaging device, and hence, an observation image corresponding to the light quantity ratio may be obtained. In other words, the illumination light suitable to diagnosis may be used for illumination, and desired tissue information of organism tissue may be obtained in a clearer state.

(14) The endoscope device according to (13), further including: light source controlling means that allows at least the first light source and the second light source to emit light within one frame of the picture signal of the imaging device.

According to this endoscope device, since an image is captured by the imaging device with the respective light sources allowed to emit light within one frame of the picture signal, an observation image in which the observation target region is irradiated with the light emitted from all of the plurality of light sources may be obtained.

(15) In the endoscope device according to (14), the light source controlling means allows at least the first light source and the second light source to emit light at different timing within one frame of the picture signal of the imaging device.

According to this endoscope device, there is no need for the respective light sources to simultaneously emit light, and hence, a burden on a subject and the power consumption of the device may be suppressed.

(16) The endoscope device according to any of (13) to (15), further including: image processing means that generates a display observation image based on the picture signal output from the imaging device; and displaying means that displays information including the display observation image.

According to this endoscope device, since the displaying means is made to display information of the picture signal supplied from the imaging device, the observation image may be easily checked and endoscopic diagnosis may be more smoothly performed.

(17) In the endoscope device according to claim 16, the displaying means simultaneously displays, in one screen: first image information obtained under visible light including the light emitted from the first light source and excited light emitted from the wavelength converting member; and second image information obtained under illumination light including the light emitted from the second light source in addition to the visible light.

According to this endoscope device, the first image information corresponding to an observation image obtained by using the visible light with a large wavelength band as the illumination light and the second image information corresponding to an observation image obtained by using the illumination light including narrow band light are simultaneously displayed in one screen of the displaying means. Therefore, a general observation image and an image in which specific information is enhanced may be easily compared with each other for the observation.

(18) In the endoscope device according to (16) or (17), the displaying means simultaneously displays, in an overlapped manner: first image information obtained under visible light including the light emitted from the first light source and excited light emitted from the wavelength converting member; and second image information obtained under illumination light including the light emitted from the second light source in addition to the visible light.

According to this endoscope device, the general observation image and the image in which the specific information is enhanced are displayed in an overlapped manner, so as to be easily compared with each other for the observation.

(19) The endoscope device according to any of (13) to (18), further including: memory means that stores information including the observation image output from the image processing means, the memory means storing the observation image in relation to the light quantity ratio.

According to this endoscope device, since the observation image is recorded in relation to the light quantity ratio set in capturing the observation image, the application range of the observation image may be increased, so that, for example, a recorded observation image may be subjected to image processing in accordance with a light quantity ratio set in capturing it.

INDUSTRIAL APPLICABILITY

According to the lighting device for an endoscope and the endoscope device of this invention, desired tissue information of organism tissue may be obtained in a clearer state suitable to diagnosis in observation of the organism tissue by using white light or special light of a specific wavelength band.

The present invention is not limited to the aforementioned embodiment but modifications and variations occurring to those skilled in the art on the basis of the description given herein and other known techniques are intended to be covered by the appended claims.

The present application is based on Japanese Patent Application No. 2009-159962 filed on Jul. 6, 2009, the entire contents of which are herein incorporated by reference.

DESCRIPTION OF REFERENCE NUMERALS 11 endoscope
13 control unit
15 display part
17 input part
19 endoscope insertion section
21 imaging device
23 operation section
35 tip portion
37A, 37B illuminating port
41 light source system
43 processor
45A, 45B, 45C, 45D optical fiber
51 blue laser light source (first light source)
53 violet laser light source (second light source)
55 light source control part
57 phosphor (wavelength converting member)
59 light deflecting/diffusing member
65 image processing part
67 control part
71 display screen
73 endoscope image area
75 general image switching button
77 narrow band light switching button
79 adjusting bar
81 knob
83 memory part
85 setting portion
87 selection button
89 switch (change-over switch)
91 blue-green laser light source
93 red laser light source
95 dichroic prism
97 phosphor (wavelength converting member)
100, 200, 300 endoscope device
A, B profile
B1, B2 blood vessel

The invention claimed is:

1. An endoscope device that emits illumination light from a tip portion of an endoscope insertion section to be inserted into a body cavity and outputs an observation image of an observation target region, the endoscope device comprising:
 a first light source that includes, as an emission source, a semiconductor light emitting device that emits blue light;
 a second light source that uses, as an emission source, another semiconductor light emitting device that emits violet light;
 a wavelength converting member that absorbs a part of the light emitted from the first light source to emit excited light so that white light is generated by combining the excited light and the blue light that is not absorbed by but passes through the wavelength converting member;
 a light quantity ratio changing unit that changes a light quantity ratio between the light emitted from the first light source and the light emitted from the second light source; and
 an imaging device, included in the endoscope insertion section, that captures the observation image of the observation target region irradiated with the illumination light and that outputs a picture signal of the observation image including blood vessel information,
 wherein the plurality of light sources including the first and second light sources are simultaneously turned on, and
 wherein the light quantity ratio changing unit changes the light quantity ratio so that as a component of the light emitted from the second light source in all components of the illumination light is increased, the observation image becomes an image in which information of a blood vessel included in a thin depth region of a mucosal surface layer of an organism tissue of the observation target region is enhanced, and as the component of the light emitted from the second light source is decreased, the observation image becomes an image in which information of a blood vessel included in a wide depth region spread from the mucosal surface layer to a deeper layer is shown.

2. The endoscope device for an endoscope according to claim 1,
 wherein the semiconductor light emitting device of at least one of the first light source and the second light source has an emission wavelength of 400 nm to 470 nm.

3. The endoscope device for an endoscope according to claim 2,
 wherein the emission wavelength of one of the first light source and the second light source is set to a shorter wavelength than a maximum peak wavelength of an absorption wavelength band of hemoglobin and the emission wavelength of the other is set to a longer wavelength than the maximum peak wavelength.

4. The endoscope device for an endoscope according to claim 1, further comprising:
 at least one third light source that uses, as an emission source, a semiconductor light emitting device of a different emission wavelength from the first and second light sources, with the emission wavelengths being different among the light sources.

5. The endoscope device for an endoscope according to claim 1, further comprising:
 an optical coupling unit that is disposed on an optical path extending from the first light source to the wavelength converting member and that guides the light emitted from at least the second light source together with the light emitted from the first light source to the wavelength converting member.

6. The endoscope device for an endoscope according to claim 1,
wherein the light quantity ratio changing unit changes quantities of the light emitted from the light sources independently.

7. The endoscope device for an endoscope according to claim 1, further comprising:
an input unit that is input light quantity ratio information specifying a desired light quantity ratio,
wherein the light quantity ratio changing unit respectively determines the quantities of the light emitted from the light sources for attaining the desired light quantity ratio based on the light quantity ratio information input to the input unit.

8. The endoscope device for an endoscope according to claim 7, further comprising:
a memory unit that stores a light quantity ratio table listing key information in relation to a plurality of light quantity ratios,
wherein the light quantity ratio information includes the key information, and
the light quantity ratio changing unit determines the desired light quantity ratio by referring to the light quantity ratio table based on the key information included in the light quantity ratio information input through the input unit.

9. The endoscope device for an endoscope according to claim 8,
wherein the key information comprises identification information of an operator of an endoscope device.

10. The endoscope device for an endoscope according to claim 8,
wherein the key information comprises individual identification information of an endoscope device.

11. The endoscope device for an endoscope according to claim 8,
wherein the input unit comprises a change-over switch for specifying any of the plurality of light quantity ratios listed in the light quantity ratio table.

12. The endoscope device according to claim 1, further comprising:
a light source controlling unit that allows at least the first light source and the second light source to emit light within one frame of the picture signal of the imaging device.

13. The endoscope device according to claim 12,
wherein the light source controlling unit allows at least the first light source and the second light source to emit light at different timing within one frame of the picture signal of the imaging device.

14. The endoscope device according to claim 1, further comprising:
an image processing unit that generates a display observation image based on the picture signal output from the imaging device; and
a displaying unit that displays information including the display observation image.

15. The endoscope device according to claim 14,
wherein the displaying unit simultaneously displays, in one screen:
first image information obtained under visible light including the light emitted from the first light source and excited light emitted from the wavelength converting member; and
second image information obtained under illumination light including the light emitted from the second light source in addition to the visible light.

16. The endoscope device according to claim 14,
wherein the displaying unit simultaneously displays, in an overlapped manner:
first image information obtained under visible light including the light emitted from the first light source and excited light emitted from the wavelength converting member; and
second image information obtained under illumination light including the light emitted from the second light source in addition to the visible light.

17. The endoscope device according to claim 1, further comprising:
a memory unit that stores information including the observation image output from the image processing unit,
wherein the memory unit stores the observation image in relation to the light quantity ratio.

* * * * *